(12) United States Patent
Singru

(10) Patent No.: US 12,048,797 B2
(45) Date of Patent: Jul. 30, 2024

(54) VENTRICULAR DECOMPRESSION AND ASSISTING APPARATUS

(71) Applicant: Kanha Vijay Singru, Pune (IN)

(72) Inventor: Kanha Vijay Singru, Pune (IN)

( * ) Notice: Subject to any disclaimer, the term of this patent is extended or adjusted under 35 U.S.C. 154(b) by 308 days.

(21) Appl. No.: 16/970,609

(22) PCT Filed: Apr. 3, 2019

(86) PCT No.: PCT/IN2019/050275
§ 371 (c)(1),
(2) Date: Aug. 17, 2020

(87) PCT Pub. No.: WO2019/193604
PCT Pub. Date: Oct. 10, 2019

(65) Prior Publication Data
US 2021/0085955 A1    Mar. 25, 2021

(30) Foreign Application Priority Data

Apr. 6, 2018   (IN) .............................. 201821013121

(51) Int. Cl.
*A61M 1/36* (2006.01)
*A61M 25/00* (2006.01)
(Continued)

(52) U.S. Cl.
CPC ...... *A61M 1/3659* (2014.02); *A61M 25/0041* (2013.01); *A61M 25/0606* (2013.01);
(Continued)

(58) Field of Classification Search
CPC .............. A61M 1/3659; A61M 1/3621; A61M 25/0067; A61M 25/0068; A61M 60/183;
(Continued)

(56) References Cited

U.S. PATENT DOCUMENTS

| | | | | |
|---|---|---|---|---|
| 4,985,014 A | * | 1/1991 | Orejola | A61M 60/117 600/16 |
| 5,011,469 A | * | 4/1991 | Buckberg | A61M 1/3644 604/6.11 |

(Continued)

FOREIGN PATENT DOCUMENTS

WO         9515192 A1      6/1995

OTHER PUBLICATIONS

International Search Report dated May 20, 2019, for International Patent Application No. PCT/IN2019/050275.

*Primary Examiner* — Susan S Su
*Assistant Examiner* — Meagan Ngo
(74) *Attorney, Agent, or Firm* — Renner, Otto, Boisselle & Sklar, LLP

(57) ABSTRACT

Disclosed is a ventricular decompression and assisting apparatus (100). The apparatus (100) includes a pigtail and a catheter that is introduced percutaneously into a femoral/radial/brachial vein or artery and is advanced into the ventricle where blood is drawn and mechanically pumped back with an external blood pump (40) and pumped back downstream into the aorta (2) or venous system or the pulmonary artery using another suitable catheter from a second access into the femoral/radial/brachial artery or any vein and with tip thereof positioned at a desired location thus forming a ventricular vent loop. The desired cardiac circulation is maintained with smart pumping, monitoring and control while relieving the load on the heart muscle to rebuild strength thereof. The apparatus (100) provides user friendly simplified approach to ventricular venting and unloading as a means for mechanical circulatory support of the left heart, right heart or both circulations even simultaneously.

15 Claims, 8 Drawing Sheets

(51) Int. Cl.
  *A61M 25/06* (2006.01)
  *A61M 60/113* (2021.01)
  *A61M 60/117* (2021.01)
  *A61M 60/232* (2021.01)
  *A61M 60/268* (2021.01)
  *A61M 60/279* (2021.01)
  *A61M 60/38* (2021.01)
  *A61M 60/515* (2021.01)
  *A61M 60/546* (2021.01)
  *A61M 60/554* (2021.01)
  *A61M 60/851* (2021.01)

(52) U.S. Cl.
  CPC ......... *A61M 60/113* (2021.01); *A61M 60/117* (2021.01); *A61M 60/232* (2021.01); *A61M 60/268* (2021.01); *A61M 60/279* (2021.01); *A61M 60/38* (2021.01); *A61M 60/515* (2021.01); *A61M 60/546* (2021.01); *A61M 60/554* (2021.01); *A61M 60/851* (2021.01)

(58) Field of Classification Search
  CPC .............. A61M 60/178; A61M 60/117; A61M 25/1002; A61M 1/3666; A61M 60/851; A61M 1/1565; A61M 1/362265; A61M 5/16881; A61M 25/0075; A61M 25/0074; A61M 2025/0076–0078; A61M 25/0041; A61M 25/0606; A61M 60/279; A61M 60/515; A61M 60/546; A61M 60/554; A61M 2205/0294; A61M 2039/224; A61M 60/892

See application file for complete search history.

(56) References Cited

U.S. PATENT DOCUMENTS

| | | | | |
|---|---|---|---|---|
| 5,449,342 | A * | 9/1995 | Hirose | A61M 60/867 604/6.11 |
| 5,688,245 | A * | 11/1997 | Runge | A61M 60/562 600/16 |
| 2004/0034272 | A1 | 2/2004 | Diaz et al. | |
| 2005/0209502 | A1* | 9/2005 | Schmid | A61F 2/064 600/16 |
| 2010/0087773 | A1* | 4/2010 | Ferrari | A61M 60/295 604/7 |
| 2012/0328460 | A1* | 12/2012 | Horvath | A61M 60/546 417/420 |
| 2013/0072846 | A1 | 3/2013 | Heide et al. | |
| 2015/0174307 | A1* | 6/2015 | Eckman | A61M 60/196 600/17 |
| 2017/0157363 | A1* | 6/2017 | Barrish | A61M 25/0136 |
| 2017/0319774 | A1* | 11/2017 | Simundic | A61M 1/3659 |
| 2018/0161553 | A1* | 6/2018 | Samuels | A61M 25/1025 |

* cited by examiner

VENTRICULAR DECOMPRESSION AND ASSISTING APPARATUS

CROSS-REFERENCE TO RELATED APPLICATION(S)

This Application is a § 371 National Stage Application of PCT/IN2019/050275, filed on Apr. 3, 2019, which relies on and claims priority to Indian Patent Application No. 201821013121, filed on Apr. 6, 2018, the entire contents of both of which are incorporated herein by reference for all purposes.

FIELD OF THE INVENTION

The present invention relates to a medical device that is inserted into patient's body for therapeutic and diagnostic purposes and more particularly, relates to a ventricular decompression and assisting apparatus that includes percutaneous catheter based transvalvar ventricular venting loops for providing mechanical circulatory support for a short term.

BACKGROUND OF THE INVENTION

Heart failure with or without cardiogenic shock following acute myocardial infarction and Acute Coronary Syndromes, unsuccessful coronary balloon angioplasty, or even after open-heart procedure is primarily due to rapid and markedly decreased performance of the heart muscle or acute decompensated heart failure.

It is believed that, unless seriously damaged, the heart of an adequately anticoagulated hospitalized patient operating at such a reduced work load with mechanical circulatory support provided, will permit next therapy and rebuild its strength over time thus obviating the need for surgical and durable VAD (Ventricular Assist Device), possible further deterioration and death.

Venting is a method for decompressing or unloading a specific compartment of the circulation system. Typically, venting is the decompression of blood from a heart chamber. The left side of the heart is where oxygenated blood is introduced into the arterial system. The right side of the heart is where deoxygenated blood is introduced into the pulmonary system.

During cardiac catheterization, the principle of percutaneous transaortic placement of catheter for venting the heart, especially the left ventricle, is a basic procedure. This technique requires a negligible amount of time and involves the insertion of vascular access sheath (catheter) through which a pigtail catheter is retrogradely advanced over the aortic valve into the left ventricle using fluoroscopic guidance and the ventricular decompression is carried out for preventing over distention and facilitating unloading of a paralyzed and weakened heart. A second catheter is inserted to pump back this decompressed volume of blood back into the circulation by placing it into aorta or vena cava depending upon hemodynamics and using a blood pump disposed outside of the patient, to which these two catheters are connected. For the right heart MCS (Mechanical Circulatory Support), a drainage pigtail or catheter maybe placed in pulmonary artery and the suction arm pigtail/catheter maybe placed in the right ventricle or atrium.

In a compromised heart, following an acute myocardial infarction or cardiogenic shock, assisting the heart pump by decreasing its work load is the object of immediate therapeutic measures, either by drugs or mechanical devices.

Many ventricular assist devices have been developed as MCS, many of which were designed to relieve the ventricle of its work load and to enhance coronary circulation. Most of these ventricular assist devices, such as the intra-aortic balloon pump, the Archimedes pump and others like ECMO (Extracorporeal membrane oxygenation), Tandem Heart are limited to assist only the left ventricle. In many instances, however, right ventricular failure may instigate the whole catastrophic event of heart failure where selective devices like right side Impella are available. In ECMO (Extracorporeal membrane oxygenation) additional left ventricular vent has been sometimes found necessary and experimented with in multiple case reports in the medical literature. Patient immobility is usually a prerequisite and drawback to most devices. Also, the profile of the catheters has been a concern resulting in bleeding, infections or requiring surgical cut downs or surgical placement of catheters. Hemolysis and blood coagulopathy are also of concern.

Accordingly, there exists a need to provide a catheter based transvalvar ventricular venting system to reduce a work load on the heart adequately and which would be an alternate to above options and overcome the above-mentioned drawbacks.

OBJECTS OF THE INVENTION

An object of the present invention is to provide a cost effective mechanical circulatory support with any suitable type of external pump and percutaneous low profile hemocompatible catheter based transvalvar ventricular vent loop.

Another object of the present invention is to provide a right ventricular circulatory support to the patient without any left ventricular assist.

Yet another object of the present invention is to provide a left ventricular circulatory support to the patient without any right ventricular assist.

Further object of the present system is to provide a biventricular assist of both right and left ventricular circulatory support with a two-channel blood pump without any open chest surgery or surgical cut down.

One another object of the present invention is to provide a system for reduction of afterload in patients without right heart failure or dysfunction by draining the vented blood from left ventricle directly into the venous system instead of the aorta or its branches.

Another object of the present invention is to provide a vent catheter with automated pressure relief valves embedded on an exterior wall to provide an intracorporeal looping of blood circulation, automatically optimizing aortic blood flows and immediate organ perfusion despite adequate or larger venting volumes.

Additional object of this invention is to provide a smart blood pump with monitoring and control of the blood pump functions with a feedback loop from various biomedical-biochemical-hemodynamic sensors and observed echocardiographic parameters. The controller is in communication with the blood pump and detects faults either in the device system or patient related parameters and then attempts to rectify these faults using chip-based iterative computing software, endowed with artificial intelligence algorithms and deep machine learning.

Yet another object of the present invention is to provide an inflatable double toroidal balloon in the form of '8' configuration with a pigtail vent catheter near the tip to permit perfusion of the aorta by passage of intrinsic ventricular output through the two-hole torus deflatable balloon while providing anchorage and stability to the vent catheter in the left ventricle.

Another object is to convert the paracorporeal vent loop to an extracorporeal loop that can be connected to an oxygenator or hollow fiber dialyzer or ultrafiltration membrane in series when required.

SUMMARY OF THE INVENTION

Accordingly, the present invention provides a ventricular decompression and assisting apparatus. The apparatus comprises a right ventricular venting loop, a left ventricular venting loop and a two-channel smart blood pump.

The right ventricular venting loop includes a first pigtail catheter and a second catheter. The first pigtail catheter serves as a suction catheter and introduced via a venous sheath from any one of a femoral vein and an arm vein. The first pigtail suction catheter includes a tip positioned near a right ventricular apex or in a right atrium. The first suction pigtail catheter of the right ventricular venting loop includes a plurality of side holes at a level of renal veins and close to a hepatic vein to reduce back pressure in the renal veins and the hepatic veins, and to prevent a suck-down event inside the right heart to improve the renal filtration pressure and thereby urine formation and also reduce hepatic congestion independently.

The second catheter being a drainage catheter is advanced into a pulmonary artery from the right ventricle via the venous sheath. The second catheter includes a first end and a second end. The first end of the second catheter includes a fluid outflow terminal means for insertion through a blood stream of the patient to a location downstream of an inflow terminal means. The second end of the first pigtail catheter of the right ventricular venting loop is coupled to the fluid output terminal means of the pump whereby blood is withdrawn through the fluid inflow means form the heart ventricle. The second catheter of the right ventricular venting loop is preferably a balloon tipped flow directed catheter. The first suction pigtail catheter and the second drainage catheter of the right ventricular venting loop have an inner lumen size ranging from 2 mm to 8 mm.

The left ventricular venting loop includes a first pigtail catheter and a second drainage catheter. The first catheter is a suction catheter preferably an angled pigtail and the second catheter is a drainage catheter. The first pigtail catheter and the second catheter of the left ventricular venting loop have an inner lumen size ranging from 2 mm to 8 mm.

The first pigtail catheter being a suction catheter is introduced percutaneously via a femoral/radial artery or any other artery via an arterial vascular sheath. The first pigtail catheter includes a tip placed beyond the aortic valve in the left ventricle. The tip of the first pigtail catheter of the left ventricular venting loop includes a double toroidal balloon to provide anchorage and stability of the tip inside the left ventricle. Specifically, the double toroidal balloon is in the form of '8' configuration.

The second drainage catheter is introduced percutaneously into a vascular system. The second catheter includes a tip. The second drainage catheter of the left ventricular venting loop is placed in the aorta or branches thereof such that the tip is positioned in the aorta anywhere from ascending portion of the aorta up to the femoral artery. Alternatively, the second drainage catheter of the left ventricular venting loop is placed in a venous system anywhere from a vena cava to the pulmonary artery or branches thereof. The partial drainage of blood to each of aorta or arterial system and the venous system or pulmonary artery is possible and drainage fractions are controlled by a suitable 'Y' diverter.

The two-channel smart pump is disposed outside a patient for simultaneous pumping of the right and the left ventricular vent loops. The two-channel smart blood pump is actuated at a desired flow rates using a controller. The controller is adapted to monitor faults and produces an alert signal in response to the detected fault. The fault is detected and controlled using air traps, air and thrombus detectors, flow and pressure volume sensors, additional data from biosensors providing biochemical, biomarker, blood gas and related data, echocardiographic and doppler derived data, feedback warning systems and emergency pump shutdown, ventricular vent valves for prevention of excessive negative pressure and a digital software with data integration for optimal pump outputs with flow rates and for triggering of weaning mode.

The pump controller is regulated digitally by computing and analyzing objective data related to the patient with a failing heart preferably with an artificial intelligence and endowed with a deep machine learning thereby helping to provide readable prompts for monitoring and control. The data includes measurements of invasive pressure and volume data of heart chamber, and non-invasive measurements of ventricular dimensions, myocardial strain rate, ventricular systolic-diastolic and contractility parameters, in addition to patient demographics and other clinically validated data and scores, indices of ventricular contractility and functions and parameters of tissue perfusion and systemic vascular resistance.

In accordance with the present invention, the right ventricular venting loop and the left ventricular venting loop are paracorporeal ventricular vent loop that is upgraded to an extracorporeal circuit by connecting to an oxygenator with or without additional blood pumps in series with the outlet loop introduced in or near a suction arm of the blood pump.

In another aspect, the present invention provides a ventricular decompression and assisting apparatus for providing a right ventricular assist to a patient without any left ventricular assist.

In yet another aspect, the present invention provides a ventricular decompression and assisting apparatus for providing a left ventricular loop to a patient without any right ventricular assist.

In yet another aspect, the present invention provides a ventricular decompression and assisting apparatus for venting and bypassing portions of a right heart and vasculature while maintaining adequate circulation that utilizes any one of a double lumen catheter and a triple lumen catheter for a right heart circulation.

In yet another aspect, the present invention provides a ventricular decompression and assisting apparatus for venting and bypassing portions of a left heart and vasculature while maintaining adequate circulation that utilizes a single lumen left ventricular vent catheter serving as a suction arm and connected to an inlet of a blood pump.

DETAILED DESCRIPTION OF THE INVENTION

Figure 1:
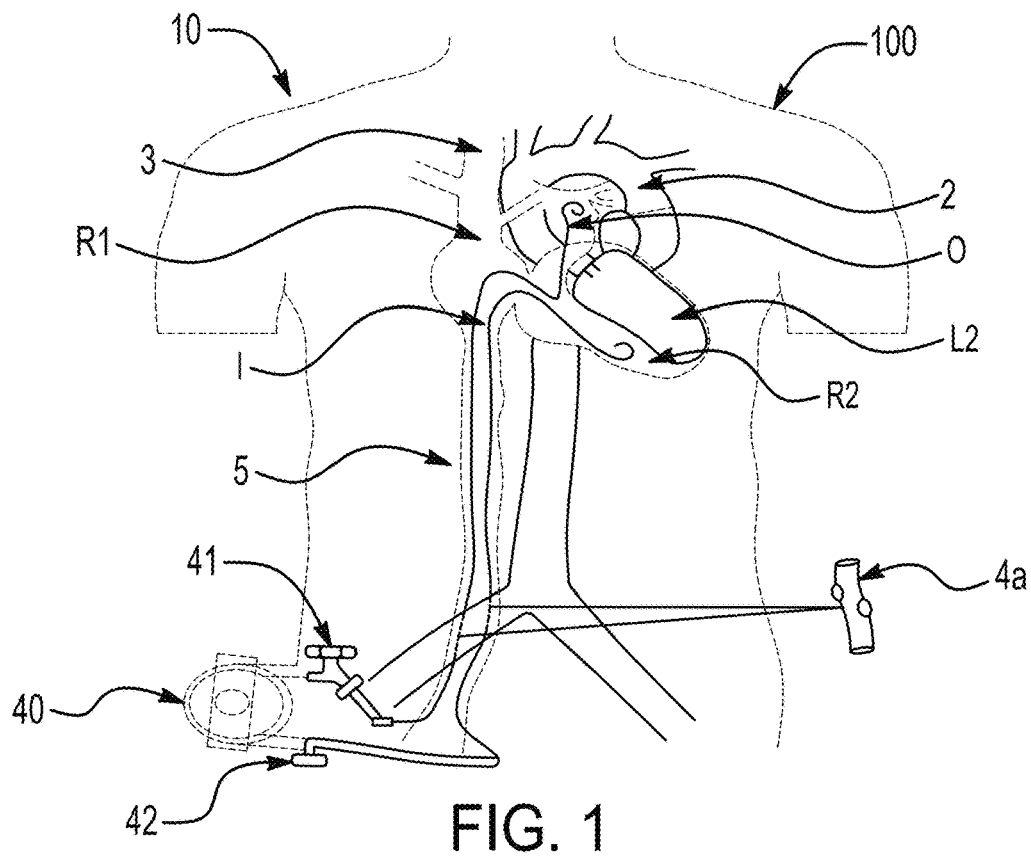
FIG. 1 shows an anatomic view of a human body illustrating the general positioning and location of two pigtail catheters for a right ventricular assistance, in accordance with the present invention.

The foregoing objects of the present invention are accomplished, and the problems and shortcomings associated with the prior art, techniques and approaches are overcome by the present invention as described below in the preferred embodiments.

This invention relates to a non-surgical method and a ventricular decompression and assisting apparatus for relieving a substantial amount of work load on the heart muscle by withdrawing a continuous flow of blood from one input chamber and mechanically pumping the blood directly into an output chamber. Accordingly, a pigtail catheter is introduced percutaneously into a femoral/radial/brachial vein or artery and is advanced into the ventricle where blood is drawn and mechanically pumped back with an external blood pump and pumped back downstream into the aorta or venous system or the pulmonary artery using another suitable catheter from a second access into the femoral/radial/brachial artery or any vein and tip thereof positioned at a desired location thus forming a ventricular vent loop. The desired cardiac circulation is maintained while relieving the load on the heart muscle to enable the muscle to rebuild strength thereof. With a steady hemodynamic state thus achieved, high risk percutaneous coronary interventions and stenting may then be safely performed to further improve the coronary circulation and hence the strength of the failing heart.

This present invention is illustrated with reference to the accompanying drawings, throughout which reference numbers indicate corresponding parts in the various figures.

| Part no | Part name |
|---|---|
| 10 | Right ventricular loop/assist |
| 20 | Left ventricular loop/assist |
| 30 | Biventricular loop/assist |
| 10d | Right ventricular assist device |
| 20d | Left ventricular assist device |
| 21d | Left ventricular assist device with double lumen catheter |
| 30d | Biventricular assist device |
| 4a | Side holes in pigtail catheter at level of renal veins |
| 4L | Side holes in pigtail catheter at level of left renal veins |
| 4R | Side holes in pigtail catheter at level of right renal veins |
| 5 | Inferior venacava |
| 3 | Superior venacava |
| 2 | Aorta |
| R1 | Right atrium |
| L1 | Left atrium. |
| R2 | Right ventricle |
| L2 | Left ventricle |
| I | Pump inflow pigtail catheter |
| O | Pump outflow pigtail catheter |
| A | Aortic Pigtail catheter |
| S | Sheath |
| 40 | Blood pump |
| 41 | Outlet |
| 42 | Inlet |
| U | Upgradable modular extensions |
| 43 | Vent valve |
| 44 | Air trap |
| 45 | Air/clot sensor |
| 46 | Doppler interrogator |
| 47 | Port |
| 48 | Filter |
| 49 | Sampling/infusion port |
| 50 | Miniaturized Single plate gate valve |
| 60 | Piezoelectrically driven micro valve opening |
| 61 | Piezo ceramic |
| 62 | Passive conductive substrate |
| 63 | Voltage source |
| 64 | On |
| 65 | Off |
| 66 | Contraction |
| 67 | Bending |
| 80 | Percutaneous TAV catheter |
| 85 | Vent catheter anchoring |
| 87 | Intralumenal vent valve |
| 88 | Lumen |
| 90 | Double toroidal balloon |
| 100 | Ventricular decompression and assisting apparatus |

Referring to FIGS. 1 to 12, a ventricular decompression and assisting apparatus (hereinafter "apparatus (100)") for venting and bypassing portions of a heart and vasculature while maintaining adequate circulation, in accordance with the present invention is shown.

Referring to FIG. 1, in one aspect, a ventricular decompression and assisting apparatus (100) for providing a right ventricular assist to a patient without any left ventricular assist in accordance with the present invention is shown. The apparatus (100) includes a right ventricular venting loop/assist (10). The right ventricular venting loop (10) includes a blood pump (40), a first pigtail catheter and a second catheter.

Figure 3:
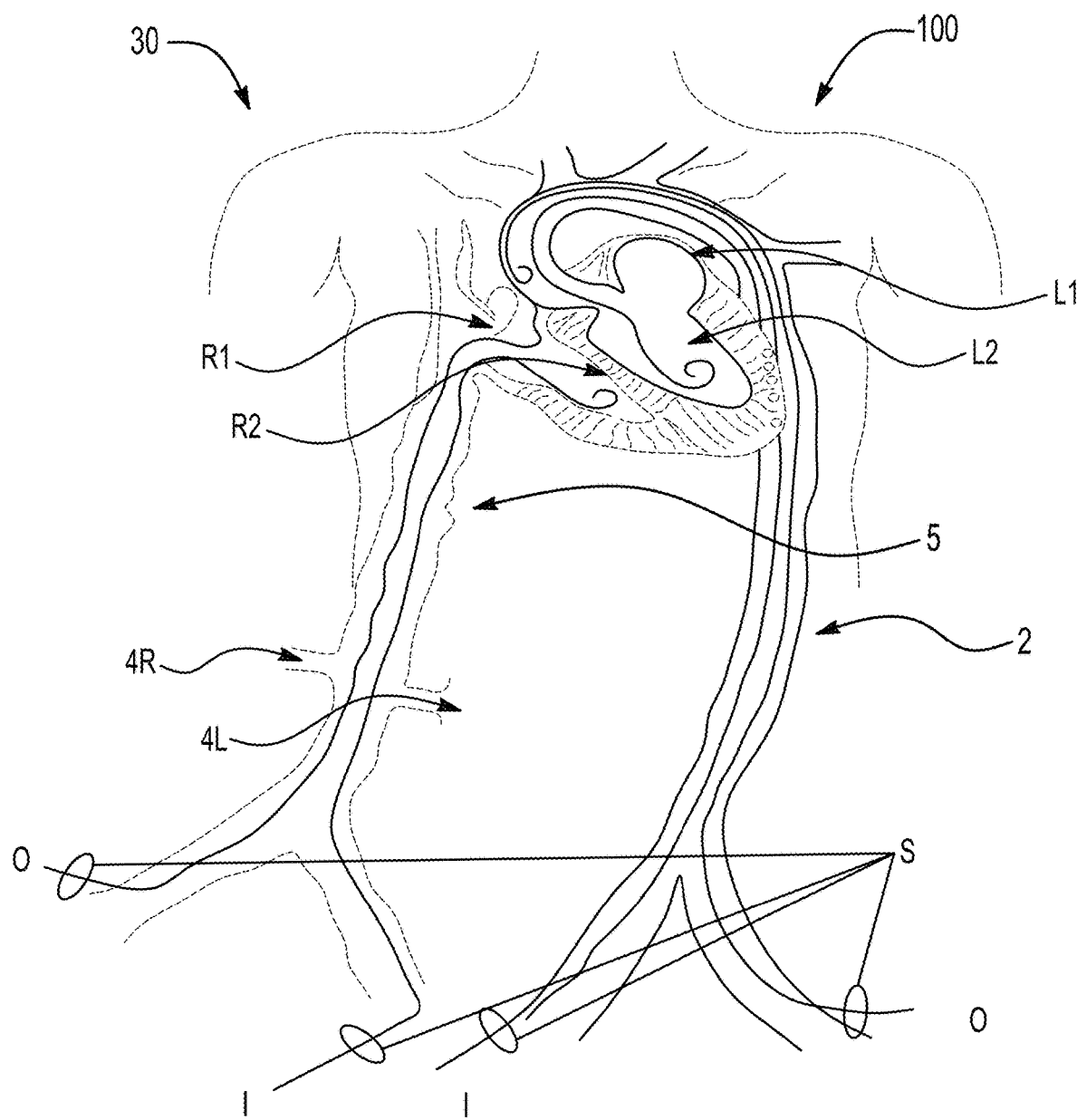
FIG. 3 shows an anatomic view of a human body illustrating the general positioning and location of two pigtail catheters for a biventricular support assistance, in accordance with the present invention.

The blood pump (40) is an external electricity driven blood pump (40) that is placed near the patient. The blood pump (40) includes a fluid inlet (42) and a fluid outlet (41). The pigtail catheters in the right ventricular venting loop (10) are introduced percutaneously by Seldinger technique into a femoral/radial/brachial artery or vein. The blood pump (40) is coupled to the pigtails/catheters in an inflow terminal (42) several inches short of an outflow terminal (41) in the end of the inner pump tubing as shown in FIG. 3. In an embodiment, the first catheter and the second catheter have an inner lumen size ranging from 2 mm to 8 mm.

The first pigtail being a pump outflow pigtail catheter (O) is introduced via a venous sheath (S) in in any one of a femoral vein and an arm vein. The first pigtail catheter includes a tip that is positioned near a right ventricular (R2) apex or a right atrium (R1). The second catheter being a pump inflow pigtail catheter (I) is advanced into a pulmonary artery from the right ventricle (R2) via venous sheath (S) in the femoral vein or any suitable venous access permitting patient mobility. Operation of the pump (40) then acts to withdraw blood from the right ventricle (R2) and return the same blood into the pulmonary artery thus forming the right ventricular venting loop or assist (10) that bypasses the pulmonic valve and relieves the heart muscle from a portion of a normal work load. The blood pump (40) is actuated at a desired flow rates using a controller. The controller is adapted to detect faults and provide monitoring and produces an alert signal in response to a detected fault that is displayed in a readable format.

Figure 2:
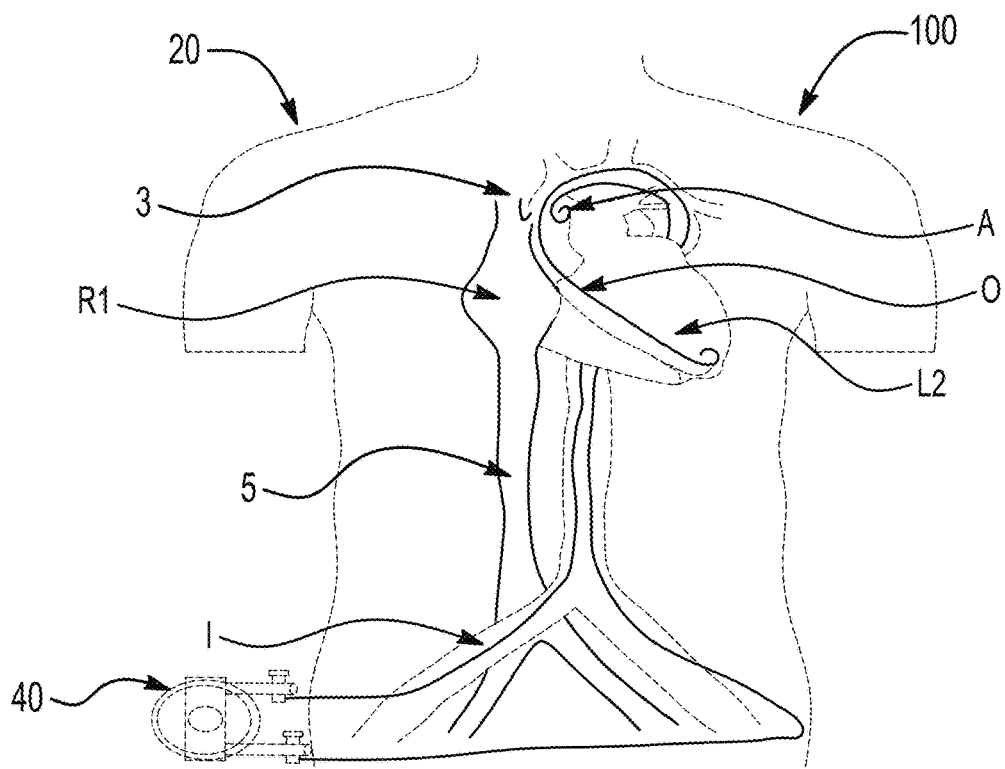
FIG. 2 shows an anatomic view of a human body illustrating the general positioning and location of two pigtail catheters for a left ventricular assistance, in accordance with the present invention.

Referring to FIG. 2, in another aspect, a ventricular decompression and assisting apparatus (100) (hereinafter "apparatus (100)") for providing a left ventricular assist to a patient without any right ventricular assist in accordance with the present invention is shown. The apparatus (100) includes a left ventricular venting loop/assist (20). The left ventricular venting loop (20) includes a blood pump (40), a first pigtail catheter and a second catheter.

The left ventricular assist (20) of FIG. 2 is similar with that of FIG. 1, the difference being that the pigtail/catheter in the left ventricular assist device (20d) is forced against the blood flow and therefore does not use an arterial balloon. The first pigtail catheter being a pump inflow pigtail catheter (I) is introduced percutaneously via a femoral/radial artery via the vascular sheath (S). The first pigtail catheter includes a tip placed beyond the aortic valve in the left ventricle (L2). The second catheter being a pump outflow catheter (O) is introduced percutaneously. The second catheter is a drainage catheter and includes a tip. In one embodiment, the second drainage catheter is placed in the aorta (2) or branches thereof such that the tip is positioned in the aorta (2) anywhere from ascending portion of the aorta (2) up to the femoral artery. In another embodiment, the second drainage catheter is placed in a venous system anywhere from a vena cava to the pulmonary artery or branches thereof. The first pigtail catheter and the second catheter of the left ventricular venting loop (20) have an inner lumen size ranging from 2 mm to 8 mm.

The blood pump (40) is coupled to the outlet (41) and inlet (42) pigtail. The blood pump (40) operates to withdraw arterial blood from the left ventricle (L2) into an inflow end of the inner tubing and return the same blood into the aorta (2) or venous circulation from the outflow end of the tubing connected to the pump outflow pigtail catheter (O), thus forming a left ventricular (L2) venting loop or assist (20) that bypasses the aortic valve to relieve the heart muscle of a portion of its normal work load and serves the purpose of a paracorporeal circulation in addition to the intrinsic cardiac output in parallel. In accordance with the present invention, partial drainage of blood to each of aorta (2) or arterial system and the venous system or pulmonary artery is possible and drainage fractions is controlled by a suitable 'Y' diverter.

Figure 7:
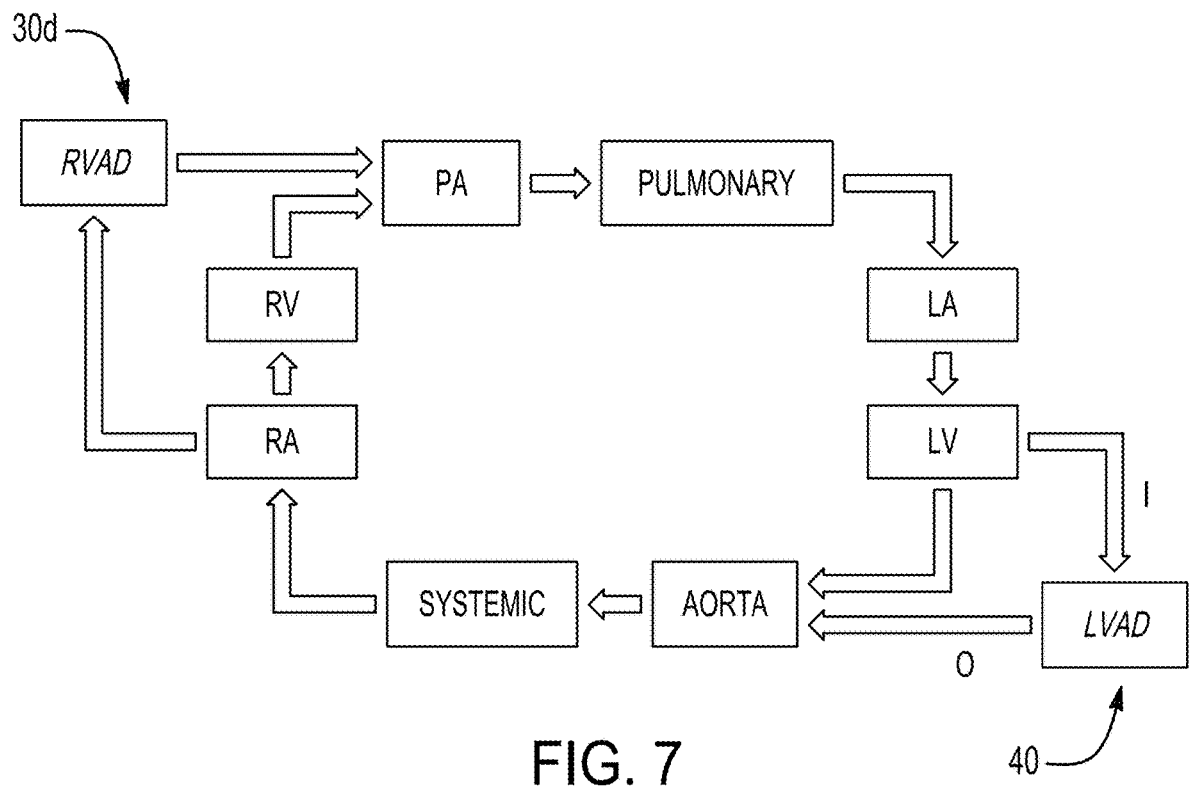
FIG. 7 shows a schematic view of a biventricular support arrangement, in accordance with the present invention.

Referring to FIGS. 3 and 7, in another aspect, a ventricular decompression and assisting apparatus (hereinafter "apparatus (100)") for venting and bypassing portions of a heart and vasculature while maintaining adequate circulation, in accordance with the present invention is shown. Specifically, the apparatus (100) is a biventricular support device (30d) with a two channel pump (40) that constitute a biventricular vent loop for treatment of a few patients which require the application of both left and right ventricular assist devices (10d and 20d respectively). The apparatus (100) comprises a right ventricular venting loop (10), a left ventricular venting loop (20) and a two-channel pump (40).

The right ventricular venting loop (10) includes a first pigtail catheter and a second catheter. The first pigtail catheter serves as a suction catheter and introduced via a venous sheath (S) from any one of a femoral vein and an arm vein. The first pigtail suction catheter includes a tip positioned near a right ventricular apex or in a right atrium (R1). The first suction pigtail catheter includes a plurality of side holes at a level of renal veins (4a) and close to a hepatic vein to reduce back pressure in the renal veins and the hepatic veins, and to prevent a suck-down event inside the right heart to improve the renal filtration pressure and thereby urine formation and also reduce hepatic congestion independently.

The second catheter being a drainage catheter is advanced into a pulmonary artery from the right ventricle (R2) via the venous sheath (S). The second catheter includes a first end and a second end. The first end of the second catheter includes a fluid outflow terminal means for insertion through a blood stream of the patient to a location downstream of an inflow terminal means. The second end of the first pigtail catheter of the right ventricular venting loop is coupled to the fluid output terminal means of the pump (40) whereby blood is withdrawn through the fluid inflow means form the heart ventricle. The second catheter of the right ventricular venting loop is preferably a balloon tipped flow directed catheter. The first suction pigtail catheter and the second drainage catheter of the right ventricular venting loop have an inner lumen size ranging from 2 mm to 8 mm.

The left ventricular venting loop includes a first pigtail catheter and a second drainage catheter. The first catheter is a suction catheter preferably an angled pigtail and the second catheter is a drainage catheter. The first pigtail catheter and the second catheter of the left ventricular venting loop have an inner lumen size ranging from 2 mm to 8 mm.

Figure 12:
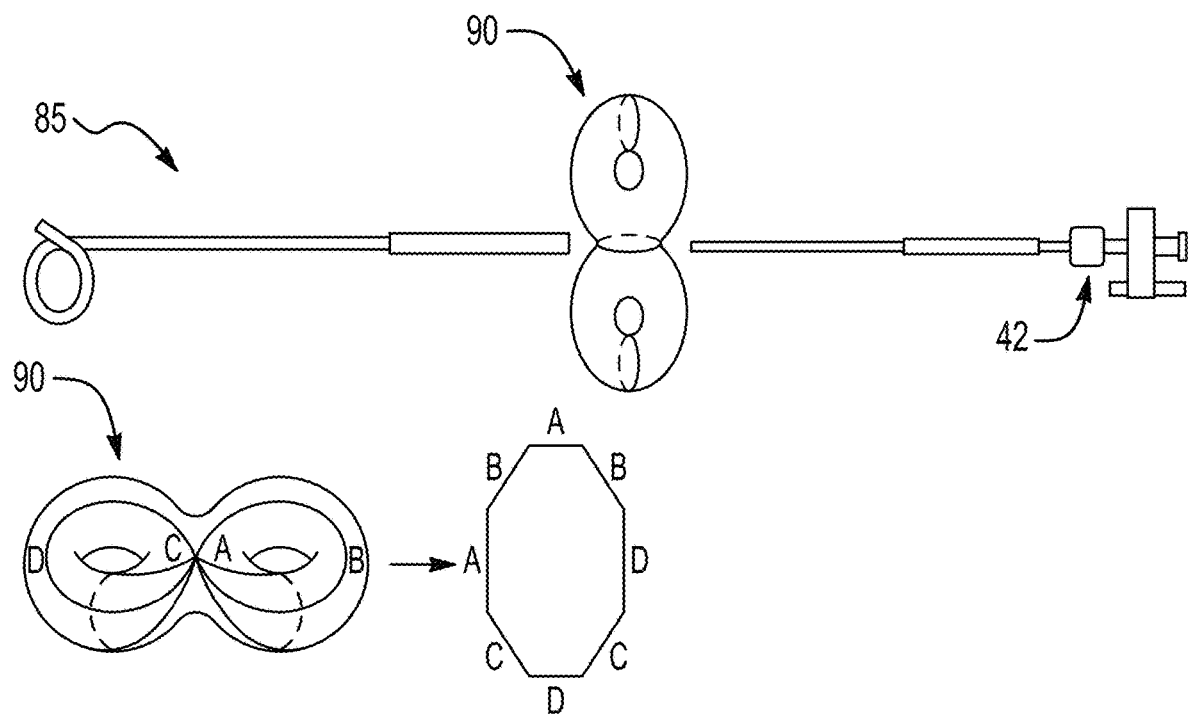
FIG. 12 shows a schematic representation of vent catheter anchoring, in accordance with the present invention.

The first pigtail catheter being a suction catheter is introduced percutaneously via a femoral/radial artery or any other artery via an arterial vascular sheath (S). The first pigtail catheter includes a tip placed beyond the aortic valve in the left ventricle (L2). The tip of the first pigtail catheter of the left ventricular venting loop includes a double toroidal balloon (90) to provide anchorage and stability of the tip inside the left ventricle (L2). Specifically, the double toroidal balloon (90) is in the form of '8' configuration. The inflatable balloon serves as an anchor below the aortic valve or above the tricuspid valve. This provides the stability necessary to maintain the vent catheter tip positioned in place for a longer time without the need for repositioning of the catheter. To maintain the forward output from the intrinsic ventricular contractility, the double toroidal structure of the balloon that permits a fraction of the blood volume in the ventricle to be pumped out into the aorta (2) is provided. The cross section of the double toroidal balloon (90) is in the form of '8' configuration with the pigtail vent catheter (80) passing from a center thereof and helps in additional perfusion of the aorta (2) as shown in FIG. 12, identifying a two-hole torus with an octagon (general topography).

The second drainage catheter is introduced percutaneously into a vascular system. The second catheter includes a tip. The second drainage catheter of the left ventricular venting loop is placed in the aorta (2) or branches thereof such that the tip is positioned in the aorta (2) anywhere from ascending portion of the aorta (2) up to the femoral artery.

Alternatively, the second drainage catheter of the left ventricular venting loop is placed in a venous system anywhere from a vena cava to the pulmonary artery or branches thereof. In shock situations the second drainage catheter of left ventricular venting loop can be placed in the arterial system anywhere from ascending aorta to femoral arteries. The partial drainage of blood to each of aorta (2) or arterial system and the venous system or pulmonary artery is possible and drainage fractions are controlled by a suitable 'Y' diverter.

The 2-channel blood pump (40) fulfills the purpose of simultaneous pumping of right and left ventricular vent loops. However, in left and right ventricular devices (10d and 20d respectively) the method of use are similar and, except that the flow direction within the arterial tubing and the likelihood of a balloon tipped catheter in the right venting loop with different access points in the arterial and venous systems.

In yet another aspect, the present invention provides a ventricular decompression and assisting apparatus (hereinafter "apparatus (100)") for venting and bypassing portions of a right heart and vasculature while maintaining adequate circulation. The apparatus (100) includes any one of a double lumen catheter and a triple lumen catheter for a right heart circulation.

In an embodiment, a double lumen catheter for a right heart circulation is used. The double lumen catheter is arranged in any one of a mother-in-child arrangement and a side by side arrangement. The mother-in-child arrangement includes an inner hypotube as a drainage catheter extending from a pump outflow to a pulmonary artery and an outer covering forming a first hypotube or a suction catheter extending from the right heart to the pump inflow, the suction catheter having a plurality of side-holes between the renal veins and the hepatic veins. The side by side arrangement includes two hypotubes with side holes on a suction arm hypotube between the renal and hepatic veins.

In another embodiment, a triple lumen catheter for a right heart circulation is used. The triple lumen catheter includes a distal lumen, a second lumen and a third lumen. The distal lumen is used for placement in a pulmonary artery. The second lumen ends at the level of a right ventricle (R2) or right atrium (R1) and meant for their decompression by attachment to the pump outflow pigtail catheter (O) that serves as an inlet (42) to the blood pump (40). The side by side arrangement of the three lumens at the distal end could vary as mother-child or varied as per the needs of the selected blood pump (40). The third lumen is used for drainage of blood from the inferior venacava (5) between the renal veins and hepatic veins. The third and outer most lumen harbor side holes between the two renal veins in the distal IVC and helps to reduce the congestion of the renal veins by attaching to the other end to the suction part of the right ventricle (R2) vent loop using a Y adapter/pressure or flow sensitive valve which in turn is connected to the inlet of a pump (40).

In an embodiment, the ventricular vent catheter (left and right) consists of a double or triple lumen catheter with first and second ends. The first end of the first lumen in left heart MCS (Mechanical Circulatory Support) vent catheter is a pigtail with a plurality of side holes (4a) and is required to be placed in the left ventricle (L2) and is the suction arm, being the pump outflow pigtail catheter (O) leading to the inlet (41) of the external blood pump (40). The second lumen is a side hole catheter (4a) superimposed on this pigtail with additional side-holes and serves as the drainage catheter, being the pump inflow pigtail catheter (I) connected from outlet (41) of the externally placed pump (40). The first end of this second lumen will begin cranial or superior to the aortic valve. The total cross-sectional area of the side holes should at least be more than the cross-sectional area of the second lumen of vent catheter. The arrangement may be side to side or like a mother and child catheter configuration, where the inner child catheter is the first lumen suction catheter and the outer mother lumen includes the first lumen and serves as the drainage or outlet (41) arm from the blood pump (40). This double lumen vent catheter can be placed across the aortic valve (9) in a retrograde fashion from an arterial sheath (S) over a guide wire, the proximal-most part of which is only single lumen.

In yet another aspect, the present invention provides a ventricular decompression and assisting apparatus (hereinafter "apparatus (100)") for venting and bypassing portions of a left heart and vasculature while maintaining adequate circulation. The apparatus includes a single lumen left ventricular vent catheter serving as a suction arm and connected to an inlet of a blood pump (40). The left ventricular vent catheter includes a vent valve (43) and a plurality of check valves.

Figure 9:
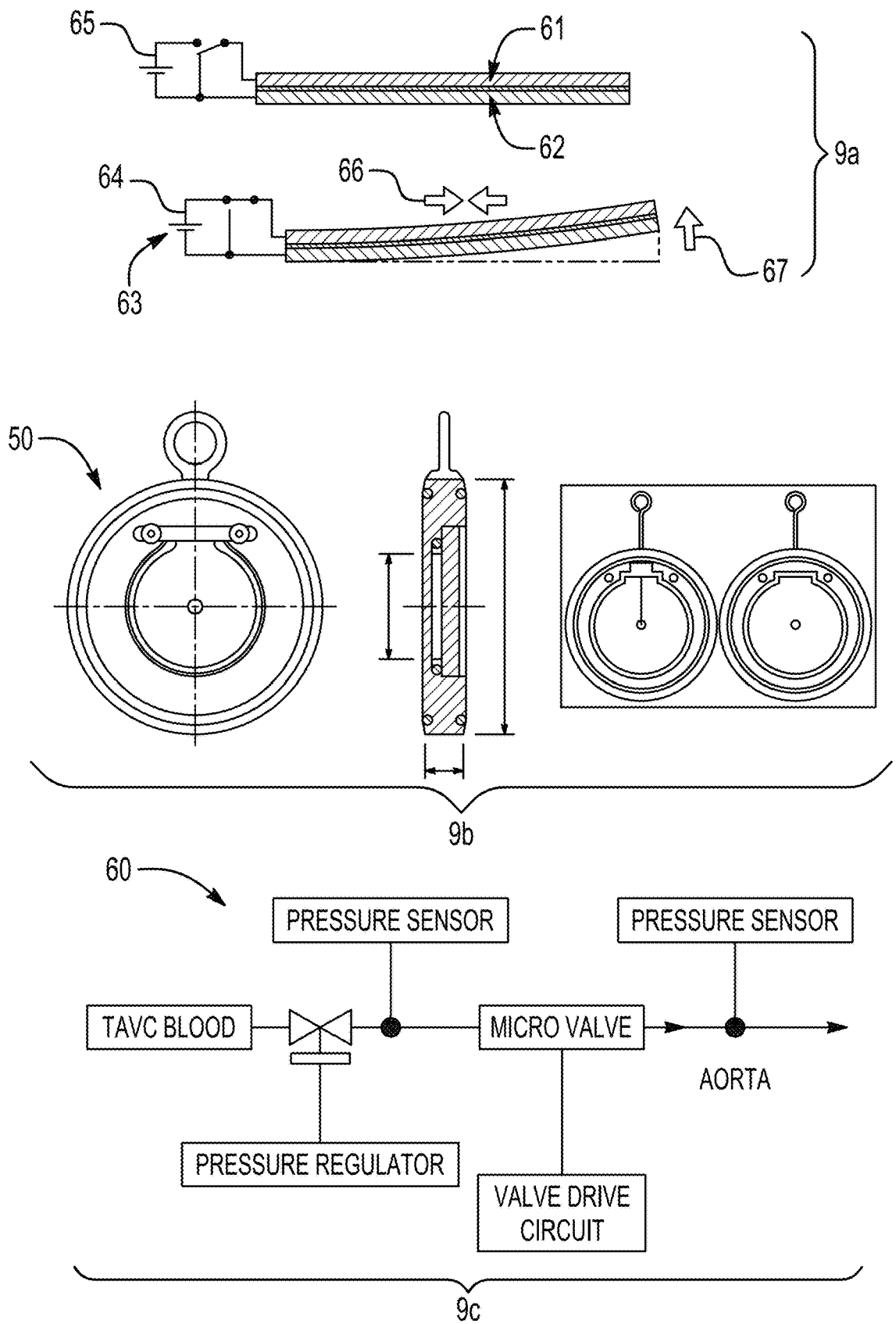
FIG. 9 shows piezoelectrically driven plate-gate type of check valve opening provided in a trans aortic vent catheter (TAVC) walls, in accordance with the present invention.
Figure 10:
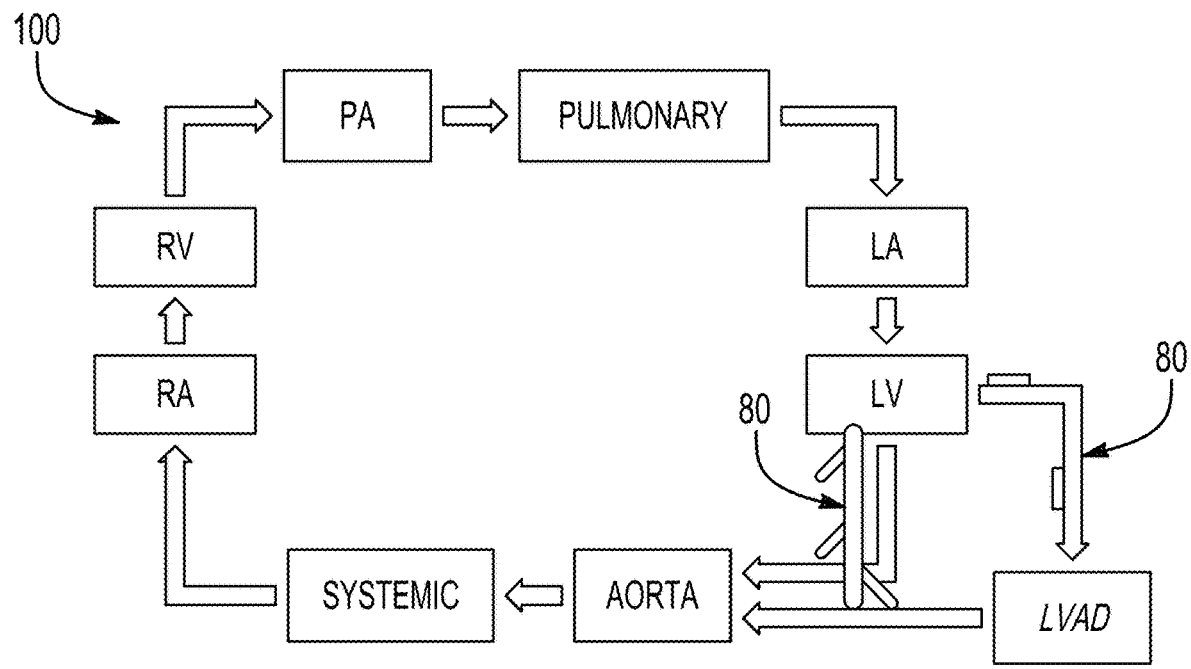
FIG. 10 shows percutaneous TAVC system with micro valves, in accordance with the present invention.

The vent valve (43) is positioned on a proximal end inside the lumen of the left ventricular vent catheter to prevent suck-down events. The plurality of check valves are configured in walls of the left ventricular vent catheter. The plurality of check valves being imbibed with robotic materials adapted to open when a pressure inside the vent catheter exceeds that of aortic blood pressure or at preset blood flow rates inside the catheter. In an embodiment, the plurality of valves are single plate gate miniaturized valves conforming to the catheter shapes that have peizoelectric microelectromechanical systems (MEMS) actuator thereon that gets activated for opening thereof as shown in FIG. 9. The actuator results in triggering valve opening or closing when the catheter pressure or blood flow exceeds or reduces to a preset limit. The trigger which is the computation of this pressure differential (or blood flow velocity and rates inside of the catheter) is preset in the valve-drive circuitry imbibed in the MEMS actuator and uses pressure sensors MEMS (or flow sensors) inside the catheter for measuring pressure (or velocity and flow) inside the catheter and also outside it for measuring the aortic blood pressure.

The plurality of valves being side valve are fused onto the wall of left ventricular vent catheter and are composed of any one of metallic-composites and carbon-composite materials possessing piezoelectric properties with their polymers that are integrated onto the catheter walls with tribological expertise and serve as a hinge and a leaf spring mechanism (welding or sintering or fusing of metallic composites or nano-onions with polymers) and enable the piezo electrically driven microelectromechanical systems (MEMS) actuator.

The apparatus (100) further comprises a peel away sheath (S) to prevent external damage to the catheter walls and the plurality of check valves and a preloaded luminal guide wire to prevent damage to the modified catheter during retrograde, transaortic insertion.

In an embodiment, the left ventricular vent catheter is a hemocompatible catheter with inner diameters ranging from 2 mm to 8 mm. The hemocompatible catheter includes side valves positioned thereon from ascending to arch of aorta (2) and if necessary in the descending thoracic and abdominal aortic portion of the vent catheter. These side valves are guarded by a miniaturized auto activated unidirectional piezoelectric valves (also functioning as pressure relief valves) as shown in FIG. 9 with predetermined triggers like set flow rates or blood pressures or blood velocity inside and/or outside the vent catheter that helps the immediate movement of the vented blood from the left ventricle (L2) into the aorta (2) and via the path of the pump outflow pigtail catheter (O) of the vent loop which is connected to the pump inlet (42).

Figure 4:
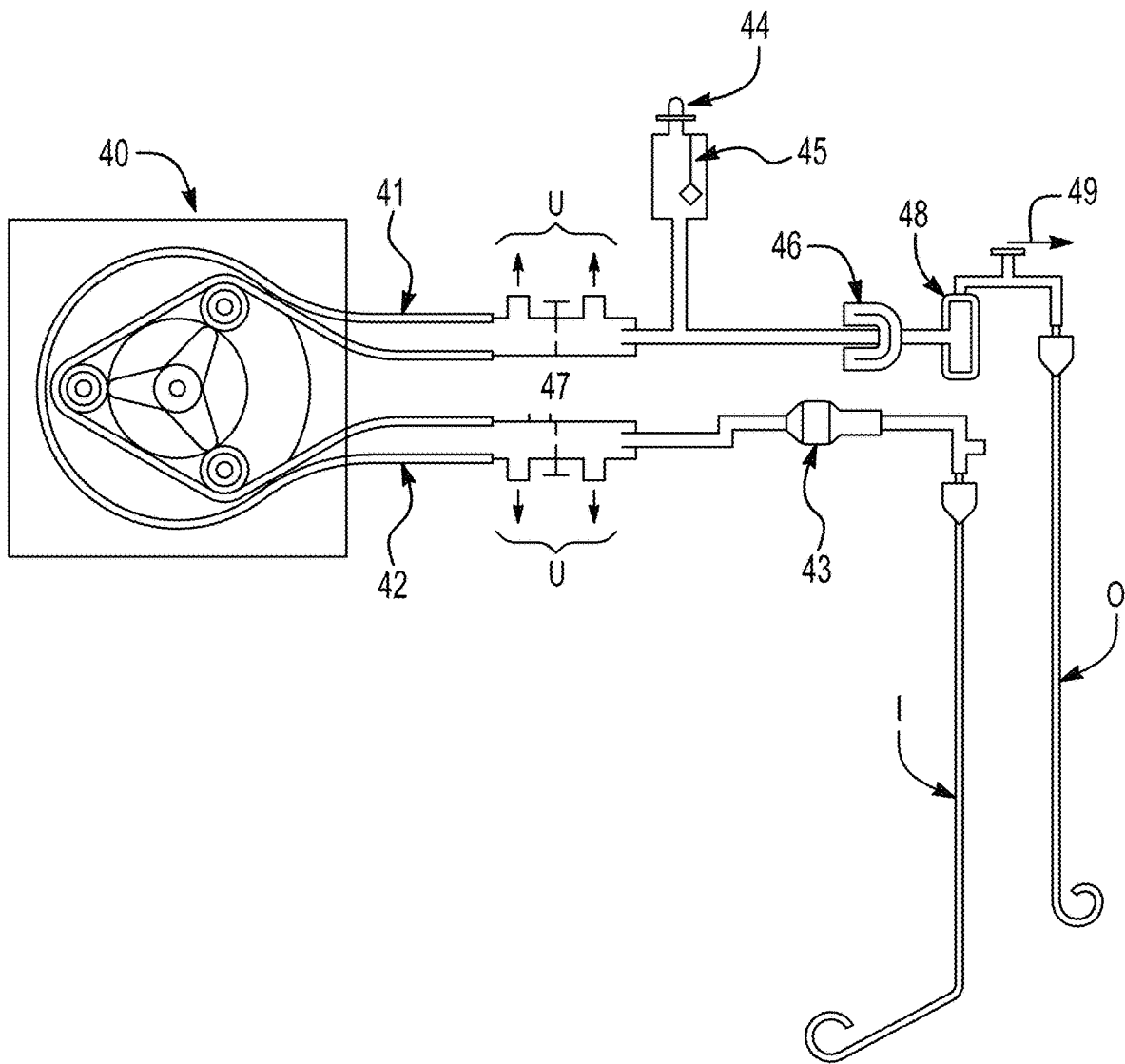
FIG. 4 shows a sectional view illustrating the arrangement of catheters with a pump, in accordance with the present invention.
Figure 5:
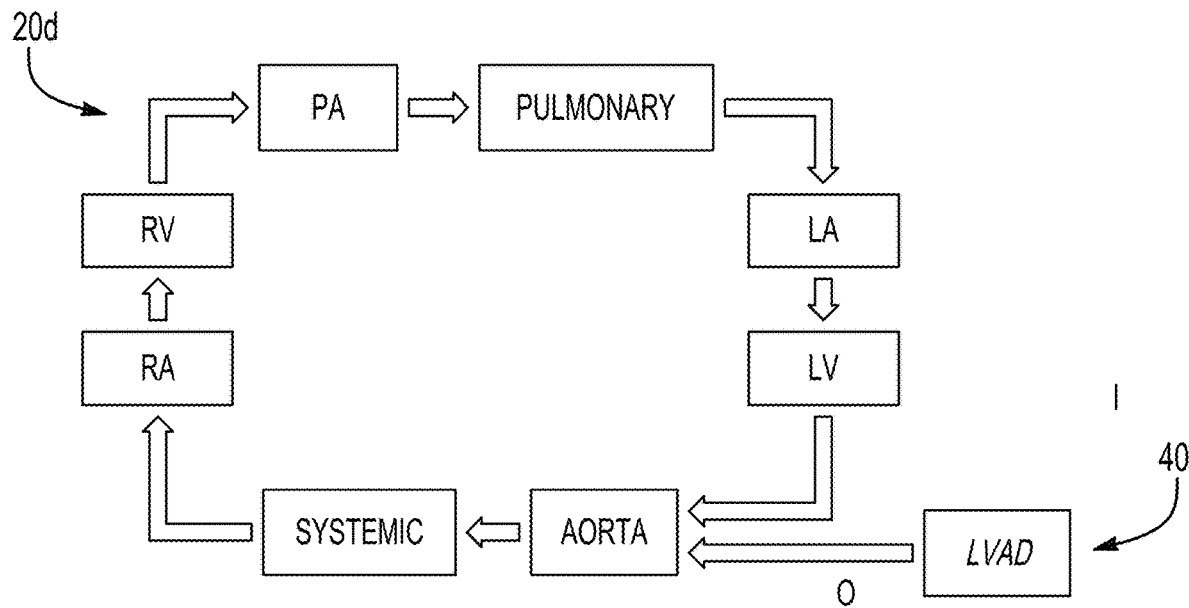
FIG. 5 shows a schematic view of a left ventricular assist device, in accordance with the present invention.
Figure 6:
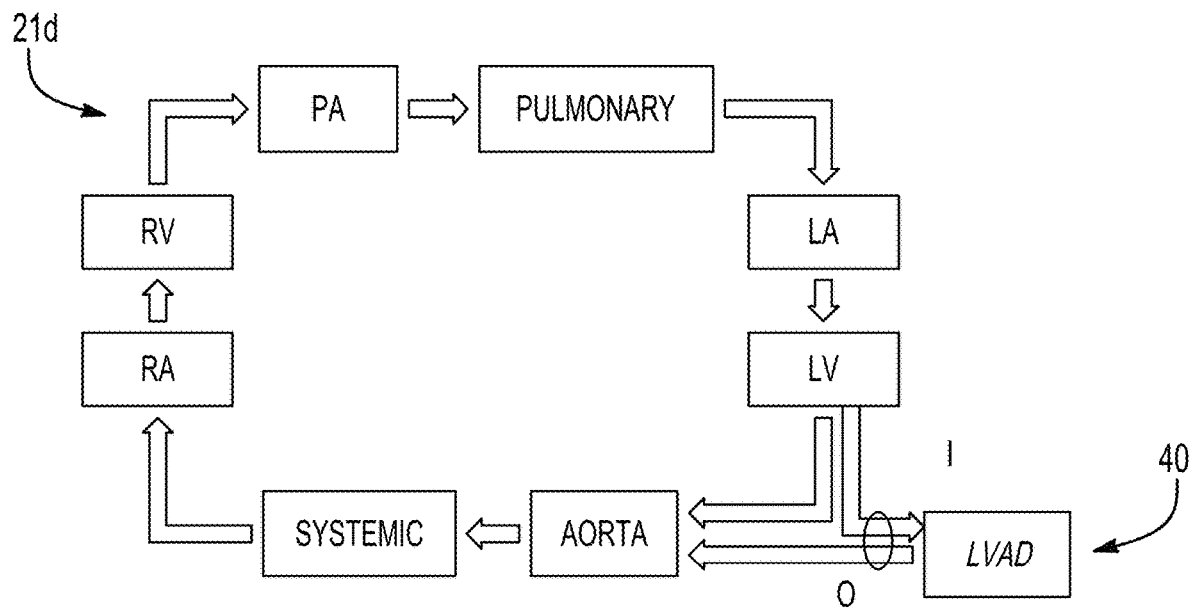
FIG. 6 shows a schematic view of a left ventricular assist device with double lumen catheter, in accordance with the present invention.
Figure 8:
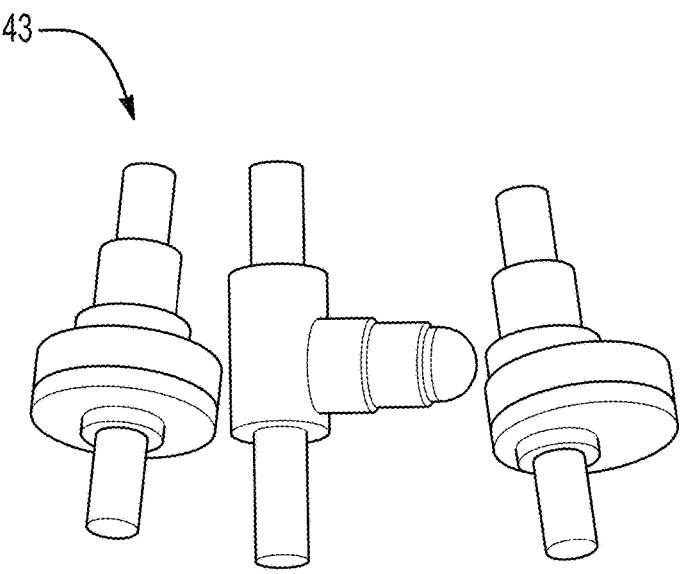
FIG. 8 shows different vent valves that are incorporated before connecting to the inlet of the blood pump, in accordance with the present invention.
Figure 13:
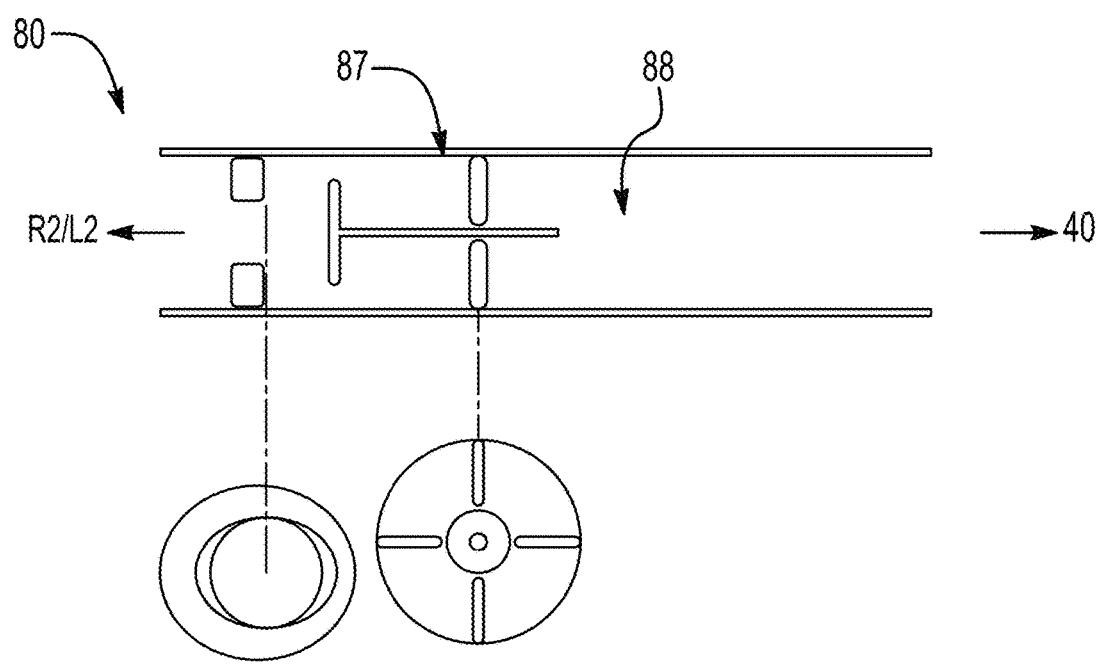
FIG. 13 shows a schematic representation of a vent valve inside the lumen of a vent catheter.

The ventricular vent valve (43) within the lumen (88) of the vent catheter (80) just after it exits the aortic valve is shown in FIG. 13. The valve (43) is a low resistance valve as it is in the pump outflow pigtail catheter (O) of the vent catheter (80) to maintain adequate forward flow in response to an externally placed blood pump (40). Alternatively, the vent valve (43) may be connected outside the body, near the inlet (42) of the pump (40) as demonstrated in FIGS. 4 and 8. In this position increasing the resistance of the vent valve (43) further augments aortic blood flow. The vent valve (43) prevents inadvertent backflow of the blood into the ventricle and also prevents tissue damage to the walls of the ventricles by limiting the development of negative pressure. The vent valve (43) also prevents thromboembolism into the vent catheter and prevents reverse flow of air emboli into the left ventricle (L2). FIGS. 4 and 8 show various vent valves (43) like Sorin (dark blue), Quest or Terumo that may be incorporated into the lumen (88) of the present invention vent catheters (80) as shown in FIG. 13.

The full pressure and full or partial flow in the venting catheter (80) at the level of side holes guarded with unidirectional miniaturized piezoelectrically actuated valves (50) embedded in the walls of the ventricular vent, which is the suction catheter that is (pump outflow pigtail catheter (O), with preset trigger points (example: vent catheter (80) pressure exceeds the aortic pressure and this generates a small current stimulating the piezoelectrically active CNT-ceramides of a plate-gate type unidirectional pressure relief Valve) is expected to directly push or divert a substantial amount of the vented cardiac blood volume into the aorta (2) during the suction of the vent loop with the external blood pump (40). The sum of cross section of the area of all the miniature pressure relief valves should exceed the area of cross section of the vent catheter. The second or distal end of this modified vent catheter may have further reduced flow and volume of blood that can be drained by the pump (40) into the venous or arterial vascular access depending upon the hemodynamic necessity.

FIGS. 9a, 9b and 9c show details of a piezoelectrically driven valve opening. The spring mechanism is provided using metallic composites or carbon nanotube CNT steel fibers fused with carbon nanotube CNT-polymers integrated with the polymers forming the vent catheter walls thus enhancing structural integrity of the "pressure relieving" plate-gate type check-valves in the vent catheter walls. Carbon nanotubes material or fullerene may also serve to securely hinge the valve on the surface of the vent catheter using nano-onions or ball bearings made of modified carbon nanotube which is integrated into the polymers.

Figure 11:
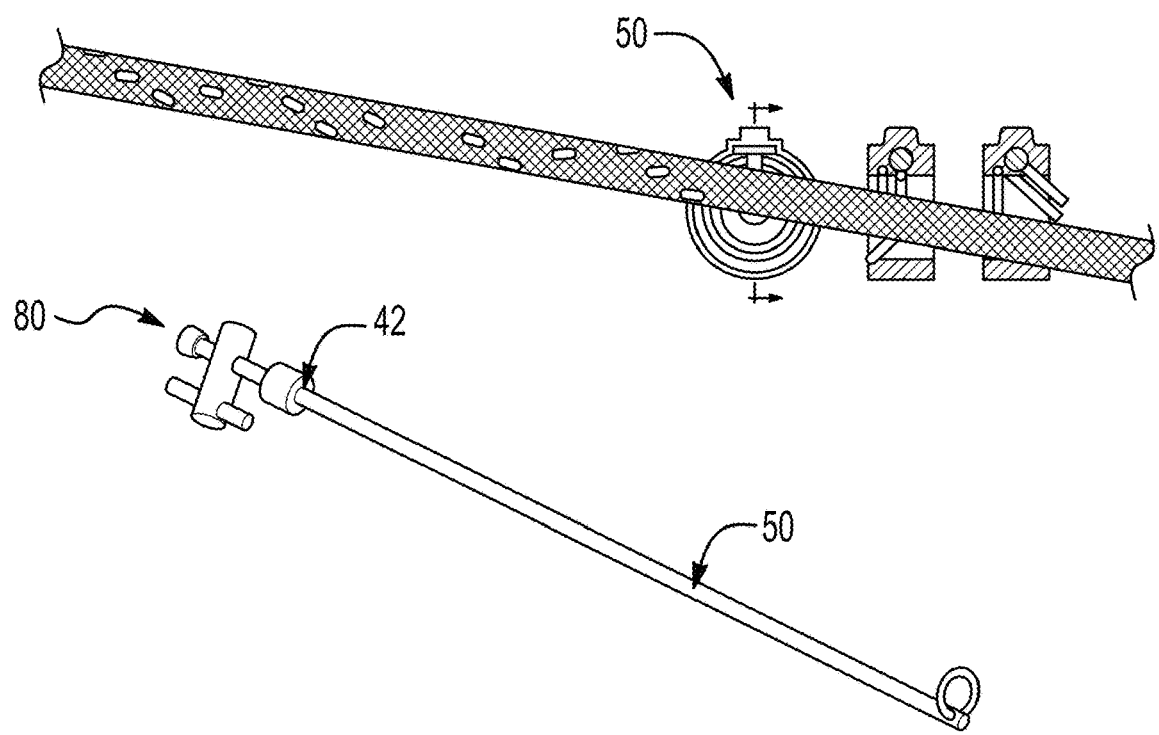
FIG. 11 shows a schematic view of a single lumen catheter with piezoelectrically driven plate-gate checkvalve, embedded on the walls of vent catheter with valve drive circuitry, in accordance with the present invention.

In accordance with the present invention, these metallic composites or CNT materials in addition to conducting electrical signals may act as pressure sensing piezoelectric material and help to gauge the various intralumenal pressures. Different CNT materials and polymers may be 3D printed and integrated to design the circuitry mechanism of the self-actuating, piezoelectrically triggered valve opening, in addition to 3D-printing the valves itself, made from the above CNT variants. These valves can be entirely 3D printed and superimposed on the walls of this catheter by fusing with the materials of the original catheter in predetermined 'gaps' or 'side-holes (4a)' as diagrammatically represented by printed dots on the catheter is shown in FIG. 11. However, it is understood here that MEMS designing and fabrication assembly with fusion methods is devised for alternative embodiments of the present invention.

In brief, an example of a single-plate gate valve (50) that functions as automated pressure-relief valves can be miniaturized and mounted on the exterior wall of the vent catheter (80) is shown in FIG. 11. Further, a piezoelectric mechanism can help to open this valve. This permits unidirectional flow from the vent catheter (80) to the aorta (2). Thus, these valves open when the vent catheter pressure exceeds the aortic pressure above a preset threshold value, and remain so open. A mechanism that can be actuated by pressure difference across the catheter valves using piezoelectric CNT-ceramides and the valve opening may be perpetuated or limited by the pressure gradient across the vent catheter (80) and the aorta (2).

FIG. 9b shows miniaturization and modifications of the single plate gate valve structure (50), using carbon nanotube CNT steel fibers as a spring and hinge integrated into the polymer of the catheter structure. The piezoelectric mechanisms are used for initiation of opening of the valve and mounting on the wall of the vent catheter (80) with valve shape conforming to that of the catheter.

Various hemodynamic scenarios are possible. Accordingly, the pump outflow pigtail catheter (O) from the vent catheter (80) may be pumped directly into venous circulation thereby facilitating additional afterload reduction especially in normotensive or hypertensive patients with a low CVP/PCWP, no evidence of right heart pathology or no features of RV failure.

Again referring to FIG. 4, the blood pump (40) is preferably driven by electricity or magnetically levitated. In an embodiment, the flow rate of the blood pump (40) is regulated with a controller. The two pigtail catheters that form the afferent and efferent part of the ventricular venting loop i.e. pump inflow pigtail catheter (I) and pump outflow pigtail catheter (O) ports, are coupled to a variable output blood pump (40). The pump (40) flow rates are adjusted according to the size of the pigtail catheter and connecting tubing diameter to provide similar outputs or flow rates. The flow rate of the pump (40) is regulated with a controller like a smart chip with additional biosensor and biochemical inputs.

The controller is in communication with the blood pump (40) and detects flows, pressures and other parameters and monitors faults and produces an alert signal in response to the detected fault. The faults may include air or thrombus in the tubing, excessive negative or positive tube pressures, blood cavitation, flow reversals, catheter obstructions, and blood flow rates markedly divergent from programmed rates, catheter displacements and leakage from the venting loop. Integrated devices (incorporated in the main device) to detect or control these faults include air traps, air and thrombus detectors, flow and pressure volume sensors, doppler interrogators, biosensors and biochemical monitors with feedback warning systems and emergency pump shutdown actuators, prevention of excessive negative pressure and tissue damage by use of ventricular vent valves and digital software with data integration for optimal pump outputs with flow rates and for triggering of weaning mode.

The controller is regulated digitally by computing and analyzing objective data related to the patient with a failing heart preferably with an artificial intelligence and endowed with a deep machine learning thereby helping to provide readable prompts for monitoring and control. The data includes measurements of invasive pressure and volume data of heart chamber, and non-invasive measurements of ventricular dimensions, myocardial strain rate, ventricular systolic-diastolic and contractility parameters, in addition to patient demographics and other clinically validated data and scores, broadly classified as central hemodynamic data, indices of ventricular contractility and functions and parameters of tissue perfusion and systemic vascular resistance. The artificial intelligence and data mining iterations and applications when applied to the apparatus (100) usage helps to auto correct, modify and reset the software of the smart chip controller to more acceptable and modern clinical endpoints.

These data can be incorporated either directly from the device (with auxiliary sensors, doppler interrogation, various biochemical and blood gas analyzers connected to this device and invasive hemodynamic measurements obtained from various portions of this device) or measured externally (parameters like echocardiographic and doppler parameters, biomarkers, myocardial strain indicators and other clinically validated data and scores to be fed into software algorithms) and analyzed into an additional computing software to automatically provide inputs for optimal and iterative adjustments of pump speeds required for achieving set clinical endpoints.

In accordance with the present invention, the fault is detected and controlled using air traps, air and thrombus detectors, flow and pressure volume sensors, additional data from biosensors providing biochemical, biomarker, blood gas and related data, echocardiographic and doppler derived data, feedback warning systems and emergency pump shutdown, ventricular vent valves for prevention of excessive negative pressure and a digital software with data integration for optimal pump outputs with flow rates and for triggering of weaning mode.

As illustrated in FIGS. 4 and 13, a vent vacuum relief valve, an air trap (44) with air/clot sensor (45), an arterial filter (48), doppler monitors (46) or probes are provided. The vent vacuum relief valve similar to Sorin, Quest or Terumo in the inlet arm (42) of the pump (40) is used to limit the negative pressure at the pigtail tip, for preventing tissue damage and to prevent inadvertent reversal of blood flow as well as prevention of gaseous emboli. The air trap (44) with the air/clot sensor (45) in the outlet arm (41) of the pump (40) is used to prevent air embolism. The arterial filter (48) at the outlet arm is used to trap emboli and particulate debris. The doppler monitors (46) or probes in the inlet (42) and outlet (41) arm are used for measurement of observed/true blood flow rate and pressure monitoring. Thus, a feedback loop is designed on the smart chip to set off alarms for obstruction or leakages in both the inlet (42) and outlet (41) vent loop. One-way infusion ports into either loop for ease of administration of concurrent drug infusions and blood sampling (49) for arterial gases and laboratory parameters are additional accessories that can be provided near the patient at the terminal ends of the pump (40) inner coupling tube as extensions. The modular upgradations (U) of the invention to include blood dialyzer and oxygenator functions in series can also be provided and facilitated by use of additional blood pumps (40).

In an embodiment, the blood pump (40) is selected from any one of a peristaltic roller pump, a membrane pump, a magnetically levitated pump and a centrifugal impeller pump. The blood pump (40) is initially programmed to maintain a flow rate of around 500 ml/minute using catheters with inner lumen sizes ranging from 2 mm to 8 mm and flow is gradually uptitrated by 500-1000 ml/minute every 5-15 minutes to achieve optimal catheter pressures and hemocompatible shear-stress rates, ventricular dimensions, pressure, myocardial strain rate, ventricular diastolic and contractility parameters based on 2D Echocardiographic and invasive data and this can be incorporated either directly (with auxiliary sensors, biochemical and blood gas analyzers connected to this device and invasive hemodynamic measurements obtained from various portions of this device including pressure-volume PV loops) or externally (measured parameters like echocardiographic parameters, biomarkers, myocardial strain indicators and others to be fed into software algorithms) into a computing software to automatically provide inputs for optimal and iterative adjustments of pump speeds. Also, the controller is programmable with a manually controllable override.

Achievement of maximal and optimal flow rates is associated with clinical improvement, reduction of pulmonary and renal congestion, improvement of blood pressure, stabilization of hemodynamics, improvement of urine output, echocardiographic parameters and other indices of cardiogenic shock and ventricular failure. These can then be computed using software iteratively, to trigger the weaning mode function of the ventricular vent loop assist device and to finally signal the removal of catheters placed invasively.

Preferably, the setup includes fixation of the blood pump (40) to a stand with preferably attachable-detachable modules, mounted on to a console trolley thereby maintaining the position of the pump (40) relative to the bed and to the catheter connections. However, it is understood here that the details of how the pump (40) is positioned relative to the patient will depend on the cannulation sites. To prevent inadvertent pulling out of the catheters, the vascular sheaths (S) and their catheters need to be sutured and secured to the skin. When vascular access is from the arms, patient mobility is possible by use of the portable blood pumps (40).

Other important features requiring attention are prime volume and pressure drop. In terms of pressure drop, it will be advantageous to minimize the pressure drop as very high negative pressure can lead to hemolysis or cavitation in the blood. So, it will usually be best to locate the pump (40) close to the catheter which brings blood from decompressed heart chamber and carries it to the pump (40). The longer tubing run can then be on the outflow side, which is the positive pressure side of the pump (40). Also, a vent vacuum relief valve similar to Sorin, Quest or Terumo may be placed in the inlet arm (42) to limit negative pressure at the pigtail tip placed in the ventricle for preventing tissue damage and also to prevent inadvertent reversal of blood flow as well as prevention of air emboli. The connecting tube could be as short as possible to minimize the priming volume to less than 100 ml. Back bleeding from the pigtail catheters to fill the pump (40) with blood and displace air and priming fluid may minimize any expected additional fluid volume infusion into the patient.

Table 1 shows relationships between pipe ID, required blood velocity for a specific blood flow rate and pressure drop that develops across the pipe.

Also shown is expected blood flow via a check valve in the wall of the tube. Expected Pump power is calculated in the last column. Assumptions and units are expressed below the table.

TABLE 1

| Pipe I.D. mm Length = 1.5 m | Blood flow Lpm | Blood velocity V = m/s | Pressure drop in Pipe (PSI/mPa/Bars) | Pressure drop across check valce (PSI/Bar) | Shear-Stress in Pipe (Pa) = 8*V*Vis ÷ D | Blood flow via check Valve Lpm 1 mm #1.5 mm & *2 mm | Pump Power, kw, +hp = Flow.lps × P(bar) ÷ 5.43 |
|---|---|---|---|---|---|---|---|
| 2 | 5 | 26.5 | 115/7.68/77 | 1115/77 | 294-424 | 1.24/2.8# | |
| 2 | 7 | 37 | 2049/14.1/141 | 2184/151 | 411-592 | 1.74/3.9# | 3.02/4.04+ |
| 2.5 | 5 | 17 | 379/2.61/26 | 373/26 | 163-218 | 0.80/1.8#/3.2* | |
| 2.5 | 7 | 24 | 691/4.76/48 | 730/50 | 213-307 | 1.1/2.5#/4.5* | 1.03/1.38+ |
| 3 | 5 | 11.8 | 158/1.08/10.9 | 153/10.5 | 87-126 | 0.55/1.25#/2.2* | |
| 3 | 7 | 16.5 | 286/1.97/20 | 299/21 | 122-176 | 0.77/1.75#/2.7* | 0.43/0.58+ |
| 3.5 | 5 | 8.7 | 75/0.51/5.2 | 72/5 | 55-80 | 0.40/0.92#/1.3* | |
| 3.5 | 7 | 12 | 136/0.93/9.4 | 141/9.7 | 77-110 | 0.56/1.27#/2.26* | 0.10/0.14+ |
| 4 | 5 | 6.6 | 40/0.27/2.7 | 38/2.6 | 37-53 | 0.31/0.7#/1.24* | |
| 4 | 7 | 9.3 | 72/0.49/4.9 | 73.7 5.08 | 52-74.4 | 0.43/0.9#/1.7* | 0.10/0.14+ |

Online Pressure calculator for straight circular tube of 1.5 m. Blood density=1060 Kg·m3
Dynamic Blood viscosity=2.78 mPa·s
Average Blood viscosity=3~4×10$^{-3}$ Pa
Roughness of tubes=0.0016 mm equivalent to new smooth rubber pipes.
Shear-stress (formula used)=8×Average Velocity of blood×Average Viscosity of blood÷Diameter tube With 2 mm tube the shear-stress is >400 Pa the upper limit for RBC hemolysis, hence it cannot be used. However, with the use of 2 mm or 1 mm pressure relieving, plate-gate smart check valves, the shear-stress will dramatically reduce even in a 2 mm tube only if the micro valves are strategically placed every 20-30 cms. This will lead to intracorporeal shunting of blood into the aorta at periodic intervals. Therefore not only the pressure drop and shear-stress reduce but also the velocity of blood, (a marker of hemolysis), and also reduced hemolysis. This will allow much higher effective blood flow volumes to be pumped out from the LV using lower profile catheters. A catheter with 2 mm, 2.5 mm and 3.0 mm, 3.5 mm and 4 mm (Up to 8 mm) inner diameter may require bench testing to check for hemocompatibility and suitability of hydrodynamics for the device in real world. Respectively, these tubes will be expected to pump 2 Lpm, 3 Lpm, 4 Lpm, 5.75 Lpm and 7 Lpm of blood from the LV approximately if at least 3 check-valves of 2 mm are placed within the first 75 cms of the tube. Smart Check valves may have 1 mm, 1.5 mm or 2 mm diameters for swing and 2-8 check valves could be imbibed on the LVAD catheter wall at strategic intervals to not only achieve organ perfusion but also to manipulate the blood flow and reduce the pump-head or pressure-drop for that segment, thus improving hemocompatibility. The pump-head or pump power required maybe calculated by additions of the respective values of all the segments of the tube to arrive at the final answer.

Table 2 shows the flow characteristics in a 3 mm tube at different blood flow rates per minute. The expected velocity of blood and shear-stress developed (indices of hemolysis) and blood flow expected from smart check valves strategically placed 25 cms from its distal tip with diameter 1 mm, 1.5 mm and 2 mm With 3-4 check valves at regular intervals, and maximum velocity of <10 m/s in any segment between two smart check valves, adequate pumping out of blood from LV cavity into aorta and also into the pump placed paracorporeally can be expected. It remains to be seen that with 3 smart check valves of 2 mm each (i.e. cross section of 2+2+2=6 mm) whether it will behave effectively as a 6 mm tube or 6 mm+3 mm=9 mm tube or some any other mathematically arrived figure regarding the blood flow rates.

Similar tables maybe setup for 2.5 mm and 2 mm tubes.

TABLE 2

| Pipe I.D. mm Length = 25 cm | Blood flow Lpm | Blood velocity V = m/s | Pressure drop in Pipe (Bars) | Pressure drop across check valve (Bar) | Shear-Stress in pipe (Pa) = 8V* Vis ÷ D | Blood flow via check Valve Lpm 1 mm/ 1.5 mm & * 2 mm |
|---|---|---|---|---|---|---|
| 3 | 1 | 2.36 | 0.11 | 0.43 | 19-28 | 0.12/0.28#/0.43* |
| 3 | 1.5 | 3.5 | 0.22 | 0.97 | 26-37 | 0.16/0.37#/0.66 |
| 3 | 2 | 4.7 | 0.37 | 1.7 | 35-50 | 0.22/0.5#/0.88* |
| 3 | 2.5 | 5.9 | 0.54 | 2.6 | 44-63 | 0.25/0.63#/1.1* |

TABLE 2-continued

|  | Blood flow Lpm | Blood velocity V = m/s | Pressure drop in Pipe (Bars) | Pressure drop across check valve (Bar) | Shear-Stress in pipe (Pa) = 8V* Vis ÷ D | Blood flow via check Valve Lpm 1 mm/ #1.5 mm & * 2 mm |
|---|---|---|---|---|---|---|
| 3 | 3 | 7 | 0.54 | 3.8 | 52-75 | 0.33/0.74#/1.3* |
| 3 | 3.5 | 8.25 | 0.97 | 5.18 | 62-88 | 0.39/0.87#/1.55* |
| 3 | 4 | 9.4 | 1.22 | 6.76 | 70-100 | 0.44/1#/1.78* |
| For Pipe L = 150 cm | | | | | | |
| 3 | 5 | 11.8 | 1.8 | 10.5 | 87-126 | 0.55/1.25#/2.2* |
| 3 | 6 | 14.1 | 2.5 | 15.1 | 105-150 | 0.66/1.5#/2.7* |
| 3 | 7 | 16.5 | 3.3 | 21 | 122-176 | 0.77/1.75#/3.1* |

For the above, Pump power in kW=Flow (Lps)×Pressure (bar)×3 (no. of check valves)÷5.43

A tube of 1.2 m is considered to be 3 segments of 25 cms each+last segment of 45 cms. After each check valve the next tube segment starts and pressure drop across the check valve is same as in the tube; hence assumptions are made that pressure drop and flow in each segment between two check valves is the same. Therefore, Pump power required for driving blood in pipe, kW=4/60×1.22×3/5.43=0.044 kW+energy required for last segment leading to the pump outlet.

Pump power for driving blood out of valves, kW=4/60×6.76×3/5.43=0.25 kW (work required against blood pressure head or 0.12 bar or 90 mmHg mean BP).

So total energy requirements as per above is 0.294 kW or 0.39 BHP+work of valve flow against aortic BP+additional energy for last segment leading to the pump outlet.

Work of valve flow against aortic BP is equal to pumping against a mean gradient of 0.12 bar and needs adjustment in calculations.

So 0.294 kW+last segment pumping energy (0.015 kW) is the pump power required in a 3 mm tube with 3 check valves (2 mm diameter) for a blood flow @ 4 lpm. Total=0.309 kW or 0.414 BHP.

Similarly, energy requirements in 3 mm catheter @ 7 lpm is 0.212 kW+1.35 kW (1.57 BHP)+Last segment pumping energy (0.43 kW); so total pump energy required=2 kW or 0.2.68 BHP.

However, it is understood here that the above calculations need supervision of a hydrodynamic engineer for further validations.

Considering the case of two 3 mm catheters with three 1 mm or three 2 mm plate-gate smart check valves. In accordance with the present invention, with three 1 mm smart check valve in the 3 mm catheter, the instantaneous intracorporeal shunting at pump speed of 4 Lpm is expected to be (0.44+0.39+0.33)=1.16 Lpm approximately. So 2.84 Lpm will be sucked out of the body via the catheter and available for an extracorporeal extension into an Oxygenator. After oxygenation, this blood may be pumped back entirely into the Aorta or the pulmonary artery thus respectively forming an A-A or A-V type of Blood Oxygenation configuration.

Alternatively, part of the blood (either 0.8 Lpm or 2 Lpm) is diverted back to Aorta and part of it (correspondingly, 2 Lpm or 0.8 Lpm) is diverted to PA. In the case of impending or absence of Cardiogenic Shock with stable MBP, 0.8 LPM to aorta and 2 LPM to PA may suffice. In the case of Cardiogenic Shock or unstable left side circulation, 2 Lpm or more can be diverted to aorta (or Systemic circulation) and the remaining 0.8 Lpm to the pulmonary artery (or venous system). A 'Y' diverter with programmable diversions of blood (by means of a graded occluder with progressive percentage reductions in blood flows and placed in either of the 'Y' arms of the diverter) or a pressure or flow sensitive valve to the arterial and venous system as described above may be suitably engineered for the same purpose. This decision making could be prompted using inputs and evolutionary Artificial Intelligence algorithms using PV loops and other collectable data or existing pump-hemodynamics of the circulatory system. Deep Machine learning may then be used to create drainage loop algorithms in the reference patient.

With three 2 mm smart check valves in the 3 mm catheter, the instantaneous intracorporeal shunting at pump speed of 4 Lpm is expected to be (1.78 Lpm+1.3 Lpm+0.8 Lpm)=3.8 Lpm. So about 200 ml blood per minute is available for an extracorporeal circuit (for oxygenation or the Ultrafiltration device) and it may be pumped back into the PA (to improve CVP) or the Aorta (if BP is low), using the 'Y' diverter appropriately. This decision making could be prompted using AI and PV loops or the then existing pump-hemodynamics of the circulatory system.

Thus the 1 mm check valve catheter will serve to perform patients with Cardiogenic Shock and hypoxia (due to Pulmonary edema) as in ADHF with shock and pulmonary edema, where an extracorporeal oxygenator is desirable; whereas the catheter with 2 mm valves will help to serve impending Cardigenic shock or its absence where pulmonary edema or hypoxia chances are remote as in High risk PCI where blood may not be required extracorporeally for oxygenation.

In accordance with the present invention, for higher pump outputs, a larger bore catheter, like a 3.5 mm ID can be used. For pumping @ 5.75 Lpm, blood velocity in a catheter segment of 25 cms is 9.98 m/s. In such a system, with three 1 mm check valves, the intracorporeal blood shunt will be (0.47 Lpm+0.44 Lpm+0.39 Lpm)=1.3 Lpm approximately with 4.45 Lpm available in extracorporeal circuit. With three 2 mm check valves, intracorporeal blood shunting will be (1.88 Lpm+1.3 Lpm+0.84 Lpm)=4.02 Lpm approximately, whereas 1.73 Lpm is shunted out in an extracorporeal circuit.

In the above examples with 3.5 mm tube catheter, if four check valves are incorporated instead of 3 then with four 1 mm valves intracorporeal shunting will be approximately 1.66 Lpm and 4.09 Lpm is available extracorporeally at pump speeds of 5.75 Lpm. With four 2 mm valves, 4.55 Lpm is shunted intracorporeally and 1.2 Lpm is approximately available extracorporeally at pump speeds of 5.75 Lpm Similar shunting values can be calculated for 1.5 mm and 2.5 mm check valves.

From the foregoing description, possible variables include quantum of intracorporeal and extracorporeal shunting during paracorporeal pumping, ID of catheter tube, diameter of check valve or number of check valves on the tube.

In accordance with the present invention, optimum values of the following are calculated using the above variables:
1) Total Pump output or speeds @ Lpm
2) Maximum speed of blood in each segment (10 m/s; a rough measure of degree of hemolysis)
3) Size of introducer sheaths for each catheter
4) Amount of blood that can be drained either into aorta or PA or both in a specific proportion.

From the foregoing discussions, it is concluded that smart check valves on the tube walls will have manifold advantages as follows:
1. Allow reductions in shear-stress developing in low profile catheters
2. Thereby lowering blood velocities which will be associated with higher blood flows in lower profile catheters
3. This results in significant reduction in pump pressure head and energy requirements.
4. This results in significantly lower risks of device-related hemolysis and this needs clinical validations.
5. Allow shunting of blood from catheter lumen (Left ventricle) to aorta directly via the check valves
6. Establishment of intracorporeal vent loop with large amount of blood flow into aorta will be associated with larger diameters of check valves and greater number of check valves. This arrangement is suitable for predominantly hemodynamic support with greater aortic BP augmentation.
7. Establishment of intracorporeal vent loop with lesser amount of blood flow into aorta resulting in greater availability of extracorporeal blood for oxygenation/UF; will be associated with smaller diameters of check valves and lesser number of check valves. This arrangement is suitable for predominantly extracorporeal pulmonary support for oxygenation with greater blood flows extracorporeally.
8. Balanced permutations and combinations with check valves' numbers and sizes will be associated with balanced hemodynamic support and modest blood flows extracorporeally available to oxygenator.

In accordance with the present invention, three different LVAD catheter configurations are thus possible with three different clinical scenarios namely:—

A] Hemodynamic support with predominant intracorporeal loop. This results in aortic BP augmentation and minimal blood reaching the pump outlet that needs to be returned to PA or Aorta. This type of catheter will be useful in impending or overt shock states where there is low probability of hypoxia and lower need for Extracorporeal Pulmonary support as in protected PCI. Example: a 3-3.5 mm diameter catheter with 3-4 check valves of 2 mm each.

B] Extracorporeal pulmonary support (Blood oxygenation) with predominant extracorporeal loop. This type of catheter is indicated when circulatory shock occurs due to non-cardiac conditions and is associated with hypoxia states as in patients' with Sepsis and ARDS with shock, cardiorenal syndromes and fluid overload states. Example: a 3-3.5 mm catheter with 3-4 check valves of 1 mm each.

C] Balanced intracorporeal and extracorporeal loops with modest hemodynamic and extracorporeal pulmonary support for blood oxygenation. This kind of LVAD catheter will provide hemodynamic support by establishing intracorporeal loops that result in adequate tissue level perfusion as well as make modest amount of blood available extracorporeally for Oxygenation using ECMO or similar devices (atleast 2 Lpm)/conventional oxygenators (atleast 3-4 Lpm). Indicated in patients with ADHF and/or cardiogenic shock with overt or impending hypoxia/pulmonary edema in the natural history of the illnessess; all etiologies associated with both these clinical scenarios. Example: A 3-3.5 mm catheter with 1-2 check valves of 2 mm each+1-2 check valves of 1 mm each.

In accordance with the present invention, the catheter sizing for the right ventricular assist device (RVAD) in mechanical circulatory support with percutaneous paracorporeal (pMCS) pumping using trans-valvar ventricular venting catheter (P3V3C) is described herein below.

For a right side pMCS catheter there will be a suction arm that leads to the pump inlet. This decompresses the right heart and extends between the RA/RV and the paracorporeally placed pump inlet. A second arm leads from the pump outlet to the PA. This is the drainage arm that drains blood into PA.

In one specific arrangement of these two arms, a mother-in-child arrangement is designed. The smaller diameter child catheter is used to cannulate the PA and serves as the pump-outlet or drainage arm of RVAD. The larger Mother catheter straddles the child like a cylinder-in-cylinder. The Mother catheter extends from right heart (RA or RV) and constitutes the suction arm.

The child catheter can be introduced singly as a PA catheter that also serves as a drainage arm of not only the RVAD but also for an LVAD loop when an LVAD is functioning alone. In case of BiVAD support a suitable 'Y' adapter is upgraded by connectors to another suitable 'W' connector to enable blood from drainage arms of both RVAD+LVAD directly into the PA.

The mother arm (suction arm), the larger of the two RVAD catheter, will be designed to enable it to slide over the child catheter. This slide will be terminated by "clips" or "locks" or "rings" designed on the walls of child catheter at the level of Right heart/RV that will prevent further sliding of the mother over the child. End holes will be created at the level of right heart. Catheter-Design engineering will need to be tested for enabling the sliding of mother over child.

Therefore the mother catheter will help to suck blood from the Right heart/RV through these end holes which will be constituted by the terminal locked area between the child and mother catheter. Additional side holes in its shaft will help to aspirate blood from RA and IVC (between Hepatic and Renal Veins). These side holes will not only reduce the RV preload but also prevent a suck-down event common with RVAD catheters. In addition, they will serve to decompress the renal veins, improve filtration pressure and similarly reduce congestion of the Hepatic tissue.

A 1.5 m long RVAD-child catheter with an inner diameter ranging from 3.3 mm-3.8 mm will have a total cylinder area between 12.83-17.01 cm2. As seen in the above Table 1, a 3 mm catheter which is 1.5 m long achieves a blood velocity of 11.8 m/s at Pump outputs of 5 Lpm, with pressure drop of <11 Bars. This 3 mm catheter has a total cylinder area of 10.60 cm2.

A 1.5 m long RVAD-mother catheter that can slide and lock over the child (PA) catheter and with lumen diameter of 4.0 mm-4.4 mm (or 4.8 mm) has a total cylinder diameter of 18.9-22.8 (27.1) cm2. So, the effective cylinder area of the mother catheter will be between 6.1 to 10.0 (or 13.8) cm2 for a 3.3 mm child and mother with 4.4 mm or 4.8 mm inner diameter respectively; this is almost similar to the cylinder area of a 3 mm or 3.4 mm catheter respectively. Therefore, the suction from a paracorporeal pump is expected to create similar blood velocities and pressure generation as a 3 mm catheter i.e. acceptable shear-stress rates. Effects of additional side-holes on the blood velocities (thus the shear-stress and indirectly the hemolysis) on the improvement in hemocompatibility need to be studied during bench and animal studies.

Whether additional upsizing is necessary for BiVAD drainage needs to be decided at full pump potentials and upper limits need to be defined for maximal LVAD drainage rates in LVAD and BiVAD configurations. With an RVAD pumping of 5 LPm and LVAD pumping of 5.75 Lpm to reduce hemolysis it will be prudent to return the LVAD blood to the aorta/arterial system.

Alternatively, above example could be replaced with a 4 mm child (PA) catheter and an 8 mm Mother (RA-RV) catheter for allowing higher blood flows safely. Alternatively a tapering 4-8 mm Mother catheter with an indwelling 3-6 mm Child-PA catheter can be designed as a single unit and introduced as a single RVAD catheter with additional blood inlets possible from the LVAD drainage arm.

In the case of patients with advanced renal failure and not responding to IVC decompression, require hemodialysis and renal replacement therapy. As an additional refinement of the apparatus (100), a hollow-fiber artificial kidney that may be incorporated in series to the inlet/outlet loops introduced near the terminal ends of the inner coupling tubing of the blood pump (40) of the apparatus (100) with the ventricular vent loop is utilized. The renal replacement therapy may then be carried out after connecting to hemodialysis machinery in series. The pump (40) speed is then rectified to overcome the resistance of blood flow at the artificial hollow fiber kidney for maintaining adequate blood flow rates.

In accordance with the present invention, the right ventricular venting loop (10) and the left ventricular venting loop (20) are paracorporeal ventricular vent loop that is upgraded to an extracorporeal circuit by connecting to an oxygenator with or without additional blood pumps in series with the outlet loop introduced in or near a suction arm of the blood pump (40). Particularly, in case of the patients with resistant pulmonary edema and resulting inadequate oxygenation of blood, the paracorporeal left ventricular vent loop is upgraded to an extracorporeal circuit by connecting to a membrane oxygenator with or without additional pumps in series to inlet/outlet loops introduced near the terminal ends of the inner tubing of the peristaltic pump (similar to a cardiopulmonary bypass or ECMO). The catheter sizes, coupling tube inner diameter and the pump speed may require to be upgraded for maintaining adequate flow rates to overcome the resistance to blood flow at the oxygenator.

In another embodiment, a complete but transient cardiopulmonary and renal replacement support is provided by the apparatus (100) that includes both an artificial kidney into the right ventricular vent loop and an oxygenator (membranous or bubble) in the left ventricular vent loop to maintain forward output of both ventricles, adequate blood oxygenation in face of lung failure with resistant pulmonary edema and renal replacement therapy for concomitant renal dysfunction by combining all the aforementioned embodiments. For this larger pigtail sizes form 2.00-8.00 mm and higher pump speeds may be required to maintain adequate blood flows. The apparatus (100) after initiation can be programmed for function escalation or down regulation with individualized functional modular format and using feedback loops and self-weaning modes by application of iterative software. Thus, a percutaneous extracorporeal ventricular vent connected to an external blood pump (40) and artificial kidney and hemodialysis machinery provides support to the cardio-pulmonary-renal compromised patients as the single device solution and hope to such patients but not limited to survivors of sudden cardiac death, prolonged cardiogenic shock and the cardio renal syndromes.

In accordance with the present invention, all the above embodiments of the apparatus (100) are available in individual and detachable modular form, into one main device, with the objective of decompressing one or both the ventricles. Also, providing adequate forward output required with profound and advanced degrees of circulatory collapse, adequate oxygenation of the blood in case of lung failure and resistant edema, and facilitating renal replacement therapy in face of renal shutdown and fluid overload, in series with the vented loops near the external blood pump (40), the paracorporeal unit or biventricular vent loop is thus upgraded to an extracorporeal circuit with single or biventricular vents, blood oxygenator and artificial kidney modules in series. Each of these functions including single/double ventricular vent can also be modified or added/upregulated or removed/subtracted/downregulated in a stepwise fashion as a modular unit of the main apparatus (100).

Advantages of the Invention

1. The apparatus (100) provides user friendly simplified approach to ventricular venting and unloading as a means for mechanical circulatory support of the left heart, right heart or both circulations even simultaneously.
2. The apparatus (100) provides bedside ambulation of the patient if percutaneous catheters are introduced through vascular sites in the arms. Additionally, this system is capable at functioning at base levels with low profile catheters introduced in the vascular systems, thus minimizing bleeding and puncture sites complications.
3. The apparatus (100) provides an easy and quick percutaneous means for establishing a large (1 to >7 liters per minute) and parallel forward cardiac output without surgical cut downs and permits perfusion of vital organs at a significantly reduced intrinsic cardiac workload.
4. The apparatus (100) by incorporating an external, portable blood pump (40) of any type or subtype, and powered externally; provides for ease of venting ventricular blood in the short-term, as a bridge to next therapy or as a bridge to bridge.
5. The apparatus (100) permits the use of such safe blood pumps (40) like peristaltic roller pumps, membrane pumps, magnetically levitated or centrifugal impeller pumps that are portable and can be designed with additional vent valves or air-traps and yet provide a large parallel cardiac output while minimizing the blood hemolysis.
6. Additionally, the present invention provides a programmable controller of the blood pump (40) with a manual override function with a feedback loop from various sensors and echocardiographic parameters. This controller is in communication with the blood pump (40) to detect faults either in the apparatus (100) or patient related parameters and attempts to rectify functions of the pump (40) using software and chip-based iterative computations.
7. The apparatus (100) additionally helps to vent blood from near the renal veins thus reducing renal venous congestion, improving renal filtration pressures, function and urine formation.
8. The apparatus (100) helps to improve and optimize aortic pressures and organ perfusion by enabling diastolic and systolic blood pressure augmentation in shock states despite adequate venting volumes, by converting a paracorporeal vent loop to an additional intracorporeal venting loop by means of automated pressure relief valves on walls of a modified vent catheter. Further aortic diastolic pressure augmentation may be possible by increasing the resistance of the vent valve (43).

9. The apparatus (100) in addition helps to drain a fraction or all the vented blood from left ventricle (L2) directly into the venous system; an option that may be used if no right heart pathology or signs of right heart failure are present or in absence of conditions that may lead to right side failure. This may additionally help to reduce afterload only in left heart failure states.

10. The inflatable double toroidal balloon (90) in the form of '8' configuration with the pigtail vent catheter passing from its center helps in catheter stability and anchorage reducing mal position and dislodgement and permits perfusion of the aorta (2) by passage of intrinsic ventricular output through the two-hole torus deflatable balloon.

11. The apparatus (100) can incorporate Hemofiltration using a hollow-fiber dialyzer or AN69 Membrane in series with the blood pump (40), thus useful for correcting fluid overload states. Hemodialysis may be also done as renal replacement therapy.

12. The apparatus (100) in addition can add an oxygenator in series with its drainage arm and with additional blood pumps, to convert to an extracorporeal oxygenation loop system when required, with ease, owing to its modular format.

13. The apparatus (100) can incorporate both a hemodialysis module and an oxygenator module both combined simultaneously, in a single patient for the treatment of cardiopulmonary-renal failure, with ease and permit stepwise downgradation of modular functions as the single device solution.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the scope of the present invention.

I claim:

1. A ventricular decompression and assisting apparatus for venting and bypassing portions of a heart and vasculature of a patient while maintaining adequate circulation therein, the apparatus comprising:
    a right ventricular venting loop comprising:
        a first pigtail catheter configured to function as a suction catheter, the first pigtail catheter configured to be introduced via a venous sheath (S) from any one or more of a femoral vein or an arm vein, the first pigtail catheter having a tip configured to be positioned near a right ventricular apex (R2) or in a right atrium (R1), and
        a second catheter configured to function as a drainage catheter and advanced into a pulmonary artery from the right ventricular apex (R2) via the venous sheath (S), the second catheter having a first end and a second end;
    a left ventricular venting loop comprising:
        a first pigtail catheter, which is a suction catheter, is configured to be introduced percutaneously via a femoral and/or radial artery or any other artery via an arterial vascular sheath (S), the first pigtail catheter having a tip configured to be placed beyond an aortic valve in a left ventricle (L2) and a proximal end positioned opposite to the tip,
        a vent positioned on the proximal end of the first pigtail catheter, the vent including a plurality of single plate gate valves made of a metallic or a carbon composite material that is piezoelectrically actuatable, wherein the plurality of single plate gate valves are configured to be actuated for opening and/or closing by piezoelectric actuation and are miniaturized to conform in shape to the first pigtail catheter such that the plurality of single plate gate valves are configured to open the vent when a pressure inside the first pigtail catheter exceeds that of an aortic blood pressure or a preset blood flow rate or pressure inside the first pigtail catheter; and
        a second drainage catheter configured to be introduced percutaneously into a vascular system, the second catheter having a tip; and
    a pump disposed outside of the patient for pumping, monitoring and control of the right ventricular venting loop and the left ventricular venting loop.

2. The ventricular decompression and assisting apparatus of claim 1, wherein the first pigtail catheter and the second drainage catheter of the right ventricular venting loop have an inner lumen size ranging from 2 mm to 8 mm.

3. The ventricular decompression and assisting apparatus of claim 1, wherein the first pigtail catheter of the right ventricular venting loop having a plurality of side holes configured to be at a level of renal veins and close to a hepatic vein to reduce back pressure in the renal veins and the hepatic veins, and to prevent a suck-down event inside a right side of the heart including the right atrium (R1) and the right ventricular apex (R2) to improve a renal filtration pressure and thereby urine formation and also reduce hepatic congestion independently.

4. The ventricular decompression and assisting apparatus of claim 1, wherein the first end of the second catheter of the right ventricular venting loop includes a fluid outflow terminal means for insertion through a blood stream of the patient to a location downstream of an inflow terminal means.

5. The ventricular decompression and assisting of claim 1, wherein a second end of the first pigtail catheter of the right ventricular venting loop is coupled to a fluid output terminal means of the pump.

6. The ventricular decompression and assisting apparatus of claim 1, wherein the second drainage catheter of the left ventricular venting loop is configured to be placed in an aorta of the patient or branches thereof such that the tip is positioned in the aorta anywhere from ascending portion of the aorta up to a femoral artery.

7. The ventricular decompression and assisting apparatus of claim 1, wherein the second drainage catheter of the left ventricular venting loop is configured to be placed in a venous system anywhere from a vena cava to the pulmonary artery or branches thereof.

8. The ventricular decompression and assisting of claim 1, wherein partial drainage of blood to each of an aorta or arterial system, or venous system of the patient and/or a pulmonary artery of the patient is possible and drainage fractions is controlled by a suitable 'Y' diverter.

9. The ventricular decompression and assisting apparatus of claim 1, wherein the first pigtail catheter and the second catheter of the left ventricular venting loop have an inner lumen size ranging from 2 mm to 8 mm.

10. The ventricular decompression and assisting apparatus of claim 1, wherein the second catheter of the left ventricular venting loop is a drainage catheter and the first pigtail catheter is a suction catheter preferably an angled pigtail.

11. The ventricular decompression and assisting apparatus of claim 1, wherein the pump is actuated at a desired flow rates using a controller, the controller is adapted to monitor faults and produces an alert signal in response to a detected fault.

12. The ventricular decompression and assisting apparatus of claim 11, wherein a fault is detected and controlled using air traps, air and thrombus detectors, flow and pressure sensors, additional data from biosensors providing biochemical, biomarker, blood gas and related data, echocardiographic and doppler derived data, feedback warning systems and emergency pump shutdown, ventricular vent valves for prevention of excessive negative pressure and a digital software with artificial intelligence software and data integration for optimal pump outputs with flow rates and for triggering of weaning mode.

13. The ventricular decompression and assisting apparatus of claim 11, wherein the controller is monitored manually or digitally by computing and analyzing objective data related to the patient with a failing heart preferably with an artificial intelligence software and endowed with a deep machine learning thereby helping to provide readable prompts for monitoring and control.

14. The ventricular decompression and assisting apparatus of claim 13, wherein objective data includes measurements of invasive pressure and volume data of heart chamber, and noninvasive measurements of ventricular dimensions, myocardial strain rate, ventricular systolic-diastolic and contractility parameters, in addition to patient demographics and other clinically validated data and scores, indices of ventricular contractility and functions and parameters of tissue perfusion and systemic vascular resistance.

15. The ventricular decompression and assisting apparatus of claim 1, wherein the right ventricular venting loop and the left ventricular venting loop are paracorporeal ventricular vent loop that is upgraded to an extracorporeal circuit by connecting to an oxygenator with or without additional blood pumps in series with an outlet loop introduced in or near a suction arm of the pump.

* * * * *